(12) United States Patent
Chen et al.

(10) Patent No.: US 10,631,396 B2
(45) Date of Patent: Apr. 21, 2020

(54) DEVICE FOR GENERATING AND DELIVERING LOW TEMPERATURE PLASMA

(71) Applicant: Nanova, Inc., Columbia, MO (US)

(72) Inventors: Meng Chen, Columbia, MO (US); Andrew Ritts, Columbia, MO (US); Zhengyu Ma, Columbia, MO (US)

(73) Assignee: NANOVA, INC., Columbia, MO (US)

( * ) Notice: Subject to any disclaimer, the term of this patent is extended or adjusted under 35 U.S.C. 154(b) by 0 days.

(21) Appl. No.: 15/925,290

(22) Filed: Mar. 19, 2018

(65) Prior Publication Data

US 2018/0270940 A1 Sep. 20, 2018

Related U.S. Application Data

(60) Provisional application No. 62/473,961, filed on Mar. 20, 2017.

(51) Int. Cl.
| | |
|---|---|
| *H05H 1/48* | (2006.01) |
| *H05H 1/00* | (2006.01) |
| *A61N 1/44* | (2006.01) |
| *A61C 19/00* | (2006.01) |
| *A61B 18/04* | (2006.01) |

(52) U.S. Cl.
CPC ............... *H05H 1/48* (2013.01); *A61N 1/44* (2013.01); *H05H 1/00* (2013.01); *A61B 18/042* (2013.01); *A61C 19/00* (2013.01)

(58) Field of Classification Search
CPC ........ A61C 19/00; A61B 18/042; H05H 1/00; H05H 1/48; A61N 1/44

USPC ..................................................... 315/111.21
See application file for complete search history.

(56) References Cited

U.S. PATENT DOCUMENTS

| 6,465,964 B1 * | 10/2002 | Taguchi | H05H 1/2406 |
| | | | 118/723 E |
| 2010/0273129 A1 * | 10/2010 | Yu | A61C 5/00 |
| | | | 433/217.1 |
| 2011/0140607 A1 * | 6/2011 | Moore | A61B 18/042 |
| | | | 315/111.21 |

(Continued)

FOREIGN PATENT DOCUMENTS

| EP | 1 096 837 A2 | 5/2001 |
| EP | 2 765 592 A2 | 8/2014 |

(Continued)

OTHER PUBLICATIONS

International Search Report and Written Opinion dated Oct. 8, 2018, in counterpart International Application PCT/US2018/023142.

(Continued)

*Primary Examiner* — Dedei K Hammond
*Assistant Examiner* — Amy X Yang
(74) *Attorney, Agent, or Firm* — Finnegan, Henderson, Farabow, Garrett & Dunner, LLP

(57) ABSTRACT

The present disclosure provides a low plasma generation system. In one implementation, the system includes a plurality of electrodes with a grounded electrode and at least one high-voltage electrode. The grounded and the high-voltage electrodes are arranged such that a tip of the grounded electrode and a tip of the at least one high-voltage electrode have a vertical-level difference.

11 Claims, 27 Drawing Sheets

(56) References Cited

U.S. PATENT DOCUMENTS

| | | | | |
|---|---|---|---|---|
| 2012/0172874 A1* | 7/2012 | Fischer | ................ | A61B 18/042 |
| | | | | 606/49 |
| 2014/0224643 A1* | 8/2014 | Collins | ............. | H01J 37/32082 |
| | | | | 204/164 |
| 2014/0276717 A1* | 9/2014 | Wan | ..................... | A61B 18/042 |
| | | | | 606/29 |

FOREIGN PATENT DOCUMENTS

| | | | | |
|---|---|---|---|---|
| EP | 2777580 A2 | 9/2014 | | |
| KR | 10-2007-0030624 | 9/2005 | | |
| WO | WO 2015/083155 A1 | 6/2015 | | |
| WO | WO-2015083155 A1 * | 6/2015 | ............. | A61C 19/06 |

OTHER PUBLICATIONS

Communication Relating to the Results of the Partial International Search and Provisional Opinion dated Jun. 25, 2018, in counterpart International Application PCT/US2018/023142 (9 pages).

* cited by examiner

DEVICE FOR GENERATING AND DELIVERING LOW TEMPERATURE PLASMA

CROSS-REFERENCE TO RELATED APPLICATIONS

This application is based upon and claims the benefit of priority from U.S. Provisional Application No. 62/473,961, filed on Mar. 20, 2017, the entire contents of which are incorporated herein by reference.

GOVERNMENT LICENSE RIGHTS

This invention was made with government support under grant No. R44DE019041 awarded by the National Institutes of Health. The government has certain rights in the invention.

TECHNICAL FIELD

The present disclosure relates generally to a device for generating and delivering plasma in atmospheric pressure and low temperature. More specifically, the present disclosure relates to a plasma hand piece that can be employed in various plasma applications such as dental and/or medical treatments.

BACKGROUND

The statements in this section merely provide background information related to the present disclosure and may not constitute prior art.

Low temperature plasma technology has been employed to initiate, promote, control, and catalyze various complex behaviors and responses in biological systems. More importantly, low temperature plasma can be tuned to achieve the desired medical effect, especially in medical sterilization, dental restoration, wound healing, and treatment of skin diseases. However, current plasma generators are generally bulky, inflexible, and requires relatively high voltage to ignite the plasma, and the plasma flame or jet generated are too large and instable in size, which poses difficulties when indirectly delivering the plasma flame to a desired but hard to reach treatment site. Furthermore, current plasma devices are generally designed for generating plasma from a signal gas (carrier gas). When mixing gases is desired for an application, a premixed gas (carrier gas mixed with reactive gas) is generally used, which results unstable plasma flame. In situ mixing of a reactive gas into carrier gases at the ignite point has not been successfully attempted.

Therefore, there is a need to provide a new and improved device for controlled generation of plasma flames or jets with significantly reduced voltage. There is also a need to provide a new and improved device for targeted delivery of low temperature plasma to an intended surface, such as a dental surface inside a patient's mouth, or a surface of a particular wound site. There is also a need to provide a new and improved device for generating low temperature plasma with in-situ mixing of gases for desired operation stability.

SUMMARY

According to one aspect of the present disclosure, a system for generating a low temperature plasma flame at a reduced voltage is provided. The system includes a plurality of electrodes, the plurality of electrodes including a grounded electrode and at least one high-voltage electrode. The grounded electrode and the at least one high-voltage electrode are arranged such that a tip of the grounded electrode and a tip of the at least one high-voltage electrode have a vertical-level difference.

According to one aspect of the present disclosure, a device, when connected with a power source and a carrier-gas supply, for generating and delivering a plasma flame to a site is provided. The device includes a housing member configured to provide gas passage, the housing member including a tip member with a tip opening at its distal end, a shaft member at its middle section, and a tubing connection member at its proximate end. The device also includes a plurality of electric lines housed in the shaft member of the housing member and connectable to the at least one power source via the tubing connection member; and a plurality of electrodes including a grounded electrode and at least one high voltage electrode, the plurality of electrodes being contained in the tip member and being attachable to the plurality of electric lines. When the device is connected to the power source and the carrier-gas supply, the carrier-gas flows from the carrier-gas supply, via the tubing connection member and the shaft member, to the tip member and is excited by the plurality of electrodes to generate the plasma flame at the tip opening.

According to one aspect of the present disclosure, a method for generating a plasma flame by a plasma generation device is provided. The plasma generation device includes a housing member, providing a carrier-gas passage, having a tip opening, and a plurality of electrodes, a plurality of electric lines, a carrier-gas passage unit, and a reactive-gas passage unit disposed within the housing member. The plurality of electrodes is disposed close to the tip opening. The method includes supplying a carrier-gas and a reactive-gas to the carrier-gas passage (i.e., the housing member) and the reactive-gas passage unit, respectively; supplying electric power to at least one of the plurality of electrodes through the plurality of electric lines; and in-situ mixing the carrier-gas and the reactive-gas at an area between the tips of plurality of electrodes.

It is to be understood that both the foregoing general description and the following detailed description are exemplary and explanatory only and are not restrictive of the claims.

BRIEF DESCRIPTION OF THE DRAWINGS

The accompanying drawings, which are incorporated in and constitute a part of this specification, illustrate example embodiments and, together with the description, serve to explain the principles of the embodiments. In the drawings.

Corresponding reference numerals indicate corresponding parts throughout the several views of drawings.

DETAILED DESCRIPTION

Figure 1A:
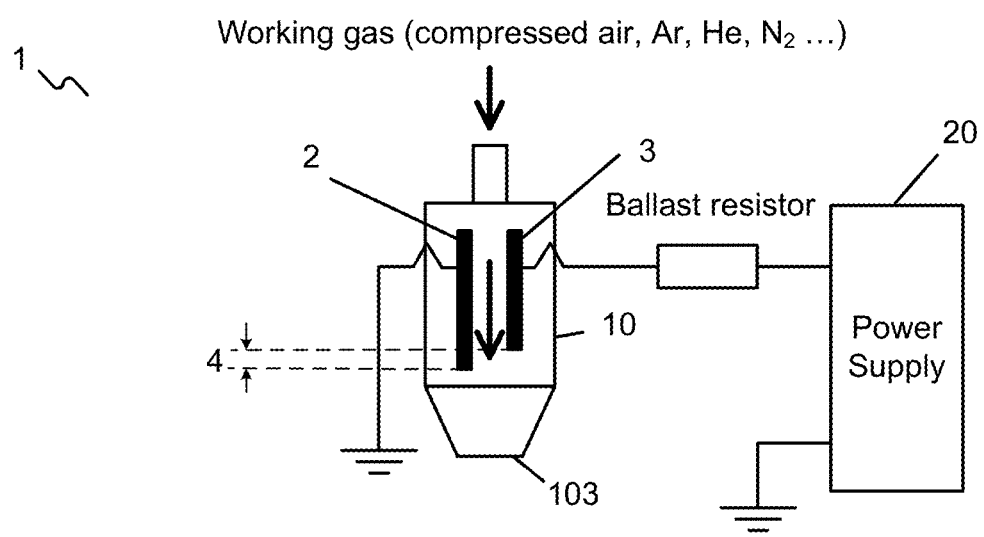
FIG. 1A is a schematic illustration of an exemplary plasma generation system with two electrodes according to an embodiment of the present disclosure.

Reference will now be made in detail to exemplary embodiments, examples of which are illustrated in the accompanying drawings. The following description refers to the accompanying drawings in which the same numbers in different drawings represent the same or similar elements unless otherwise represented. The implementations set forth in the following description of exemplary embodiments do not represent all implementations. Instead, they are merely examples of devices and methods consistent with aspects related to the appended claims.

The present disclosure addresses one or more disadvantages associated with the conventional low temperature plasma devices. In one aspect, the present disclosure provides an inventive plasma generation system for igniting and sustaining a low temperature plasma flame under reduced voltage. The plasma generation system includes a plurality of electrodes with one grounded electrode and at least one high voltage electrode, whereas the electrodes are so oriented that the tip of the grounded electrode and the tip(s) of the high voltage electrode(s) are on different vertical levels approximately 1 mm to 6 mm apart.

According to one embodiment, the system includes a pair of electrodes with the anode grounded and the cathode applied with negative high voltage, wherein the tip of the grounded electrode and the tip of cathode is approximately 1 mm to 6 mm vertically apart. With this embodiment, the cathode initially carries about −2500 V (Volts) to ignite the carrier gas and then drops to about 1000 to 1200 V to sustain the plasma flame generated. With the voltage dropping, the plasma flame is safer for clinical applications. Furthermore, preferably the electrodes are so arranged that the tip of the grounded electrode is closer to the nozzle (opening for plasma flame) to further facility the safety in a clinical application.

According to another embodiment, the system further includes an additional high voltage electrode, i.e., a trigger electrode, for releasing a single shot of pulsed signal to facilitate the plasma generation under further reduced ignition voltage. The trigger electrode may be placed in between the grounded electrode and the cathode, while the vertical placement of the tip of the trigger electrode is also between the tip of the grounded electrode and the tip of the cathode. When a trigger electrode is employed and a single shot of pulsed signal is applied during the plasma flame ignition process, the voltage of the cathode can be further reduced to enhance the clinic safety of the system.

In another aspect, the present disclosure provides a plasma generation and delivery device (i.e., a plasma brush hand-piece) for generating plasma flame, with stable and desired miniature size and shape, and precisely targeted delivery of such to an intended surface. The disclosed device, i.e., the plasma brush hand-piece, for controlled generation and targeted delivery of plasma flame, when connected with the desired power source and plasma gas supply, includes i) housing member for housing electric lines and electrodes and providing gas passage, wherein the housing member includes a tip member with a tip opening at its distal end, a shaft member at its middle section, and a tubing connection member at its proximate end, ii) plurality of electric lines housed in the shaft member and electrically connected with the power source through the tubing connection member, and iii) plurality of electrodes, with one grounded electrode and at least one high-voltage electrode, housed in the tip member and electrically connected to the electric lines. The tip of the grounded electrode and the tip of the high-voltage electrode are on the different vertical levels approximately 1 mm to 6 mm apart. After being assembled, the desired gas flows from the gas supply via the tubing connection member and the shaft member to the tip member and is ignited by the plurality of electrodes to generate plasma flame at the tip opening.

On yet another aspect, the present disclosure provides a device for generating low temperature plasma with in-situ mixing of gases for desired operation stability and clinical application. When two or more types of gas (plasma carrier-gas and at least one reactive gas) are desired in generation of low temperature plasma for a particular application (dental or medical), the reactive-gas tubes can be employed to provide passage for reactive gas to ensure its in-situ delivery to the plasma-flame generating spot, i.e., the area between tips of the electrodes. Thus, the disclosed device may further include, besides the above-mentioned elements, a reactive-gas passage unit for generating plasma flame with multiple gas supplies (i.e., the plasma carrier-gas supply and at least a preselected reactive-gas supply). The reactive-gas passage unit includes a reactive-gas line housed in the housing member. The reactive-gas line may be segmented but attachable with two sections, a proximate reactive-gas tube and a distal reactive-gas tube, whereas the proximate reactive-gas tube is housed in the shaft member, and the distal reactive-gas tube in the tip member. After being assembled, the reactive-gas can flow through the reactive-gas passage unit and be released in-situ at the electrodes (preferably at closer approximate to the grounded electrode than the high-voltage electrodes, such as the cathode) to be excited with the plasma carrier-gas. When a premixed gas is desired (instead of the in-situ mix of two gases), the distal reactive gas line may be omitted, so that the reactive-gas flows through the proximate reactive-gas tube to the tip member and is mixed with the plasma gas within the tip member to be excited by the electrodes.

More specifically, according to one embodiment, the aforesaid tip member includes a) a tip shell in hollow conical shape forming a tip chamber with a narrow tip opening and a wide tip base end, and b) a tip insert, in a conical frustum shape, tightly fitted at the tip base end. The tip insert includes a first carrier-gas opening for the passage of carrier-gas and a pair of electrode slots for attaching the electrodes. The tip member may further include a first set of electric connectors inserted in the electrode slots for connecting the electrodes with their respective electric lines. The connectors may be a pair of pin contacts or any other electrically conductive unit. When multiple gases are desired, and the reactive-gas passage unit is employed, the tip insert may further include a first reactive-gas slot for attaching the distal reactive-gas lines and connecting such to the proximate reactive-gas lines in the shaft member. Preferably, the tip shell may be designed to assume a bent curve so that the plasma flame generated at the tip opening can be easily directed to an intended and hard-to-reach surface, for instance, the dentin surface inside the cavity of decayed teeth. Furthermore, the tip member may be disposable, so that a new clean and even sanitized tip member may be employed for such application to avoid cross contamination.

According to another embodiment, the aforesaid shaft member may include a) a shaft shell in an elongated curved tubular shape forming a shaft chamber with a shaft-tip end and a shaft-connector end, b) a shaft-tip insert, fitted at the shaft-tip end, having a second carrier-gas opening aligned with the first carrier-gas opening to provide core plasma gas passage and a first pair of electric slots aligned with the electrode slots to provide connection between the electrodes and the electric lines, and c) a shaft-connector insert, fitted at the shaft-connector end, having a third carrier-gas opening for the passage of carrier-gas and a second pair of electric slots to provide connection between the electric lines and the power source. The shaft member may further include a second and third pair of electric connectors inserted in the first and second pair of electric slots, respectively, to facilitate the electric connections between the electrodes, the electric lines and the power source. Optionally, the shaft member may include a partition unit to divide the shaft chamber to separately house the electric lines to prevent accidental contact or short-circuit between the electric lines. When the reactive gas is desired and the reactive gas passage unit is employed, both the shaft-tip insert and the shaft-connector insert may further include a second and third reactive-gas slots, respectively, for attaching the proximate reactive gas lines and connecting such to the distal reactive gas line at the shaft-tip insert and to the reactive gas supply at the shaft-connector insert.

According to yet another embodiment, the aforesaid tubing connectors may include a source connector in a modified cylindrical shape with an adaptor end and a tubing end, wherein the adaptor end has a) a third pair of the electric slots with a fourth pair of electric connectors for connecting the electric lines to the power source, and b) a fourth carrier-gas opening with a gas fitting unit to connect to the carrier-gas passage to the gas supply. When the reactive gas is desired and the reactive gas passage unit is employed, the adaptor end may further include a fourth reactive-gas slot with gas fitting unit to connect the reactive-gas passage to the reactive gas supply. The tubing connectors may further include a connector collet in a hollow cylindrical shape, which after assembly may slide over the source connector and the shaft-connector end to ensure a secure attachment between the source connector and the shaft member. Optionally, the tubing connectors may also include a compression ring at the tubing end for establishing a secure connection with the source tubing. After being assembled, the components are assembled in such a manner and arrangement that the electrodes connect with their respective electric lines then the power source, the carrier-gas openings are aligned for the carrier-gas passage from the carrier-gas supply, and the reactive-gas slots are aligned with the reactive gas tubes to provide the reactive-gas passage from the reactive-gas supply, if employed.

The present disclosure relates to a system and device (i.e., a hand-piece) for controlled generation and targeted or localized delivery of a low temperature plasma flame or jet to an intended surface. The inventive system employs a plurality of electrodes (grounded electrode and at least one high-voltage electrode) with novel placement of such to reduce the voltage required to ignite and sustain the plasma flame, whereas the grounded electrode and the high voltage electrode(s) are placed with a different vertical level approximately 1 mm to 6 mm apart. The plasma flame so generated is in miniature size ranging between 5×2×2 mm to 10×3×3 mm (length×width×thickness) having a reduced temperature below 101° F. (38° C.). The inventive hand-piece provides easy handling by a user, while the hand-piece's curved and/or bent conical tip opening facilitates the generation of plasma flame in stable shape and a size suitable for localized application for even to hard-to-reach surfaces during a dental or medical procedure. The exemplary hand-piece further provides means to introduce a reactive-gas (such as, Hydrogen, Oxygen, Air, Water Vapor, Nitrogen, Chlorofluorocarbons, Tetramethylsilane, Dimethysilane, Methane, Ethane, and other gases) to the conventional plasma gas (the "carrier-gas," such as, Argon, Helium, compressed air, Nitrogen, and another inert gases) near the ignition site (e.g., near the grounded electrode) for specialized treatments or applications.

FIG. 1A is a schematic diagram of an exemplary plasma generation system with a pair of electrodes, according to one embodiment of the present disclosure. As shown in FIG. 1A, the plasma generation system, 1, includes a grounded electrode (anode), 2, a high voltage electrode (cathode), 3, whereas a tip of the grounded electrode, 2, and a tip of the cathode, 3, are arranged with a vertical-level difference, 4, ranging from approximately 1 mm to approximately 6 mm. The electrodes, 2 and 3, are contained in a plastic tube to constitute a hand-piece, 10, described in more detail below. The grounded electrode, 2, and the cathode, 3, are disposed in parallel and spaced apart from each other with a distance of less than or equal to 8 mm. In some embodiments, the grounded electrode, 2, and the cathode, 3, are horizontally spaced apart with a distance of 3 mm to 4 mm. In one embodiment, the grounded electrode, 2, is placed closer to a nozzle (a tip opening, 103, described in detail below). The plasma generation system, 1, further includes a power supply, 20, connected to the cathode, 3, via a ballast resistor. The power supply, 20, may be configured to apply, to the cathode, 3, a first negative high voltage of approximately 2000 V-3000 V at ignition, which drops to a second negative high voltage of approximately 1000 V to 1200 V after ignition.

Figure 1B:
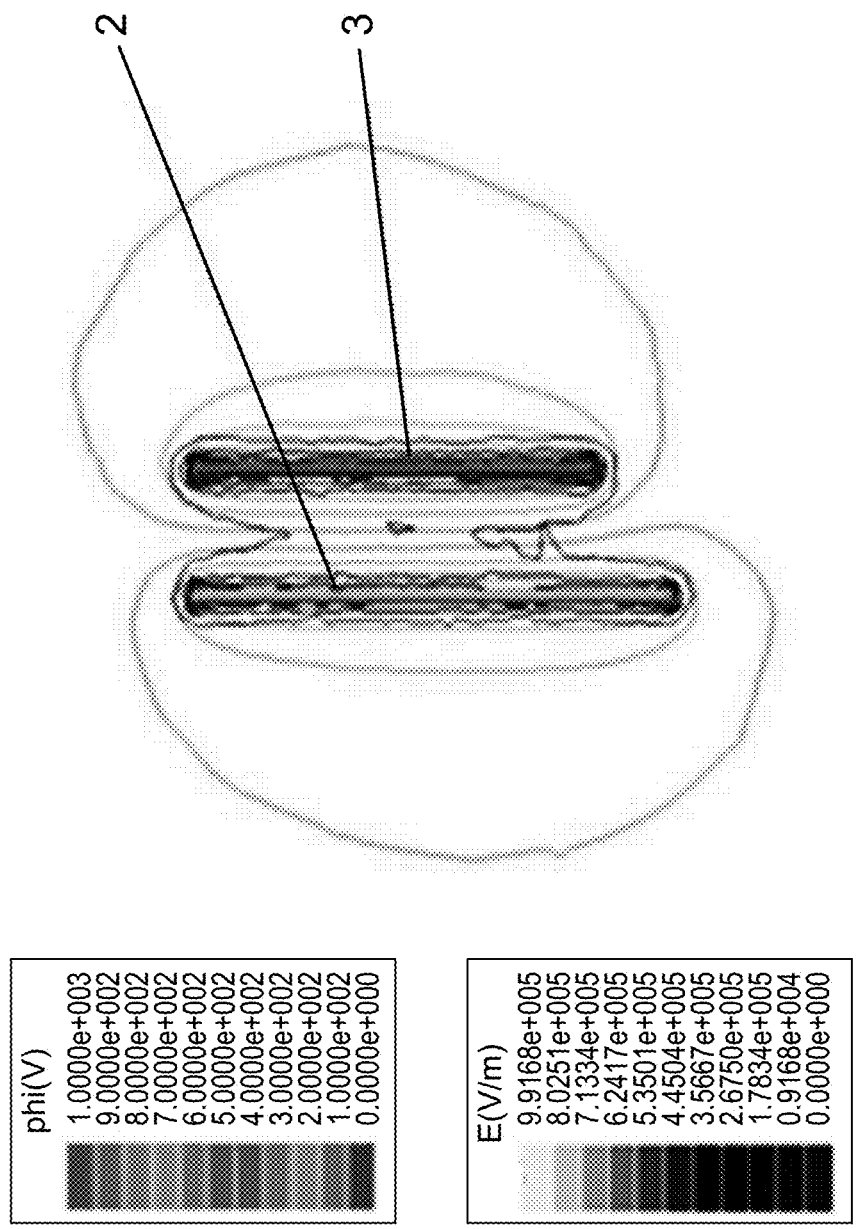
FIG. 1B illustrates an electrostatic field distribution analysis of the exemplary system in FIG. 1A.

FIG. 1B is an electrostatic field distribution analysis of the exemplary plasma generation system, 1, with two electrodes at different vertical levels. In the exemplary plasma generation system, 1, of which the electrostatic field distribution analysis is performed, the grounded anode, 2, and the cathode, 3, are 30 mm and 25 mm in length respectively, are made of platinum (or tungsten), each has a diameter of 1 mm, and are horizontally spaced apart with a distance of 8 mm. The electrostatic field analysis shows that the maximum field strength at an applied voltage of 1000 V is $8.92 \times 10^5$ V/m, which is 10% higher than the one in a comparison plasma generation system with two electrodes of equal length of 30 mm.

Figure 2A:
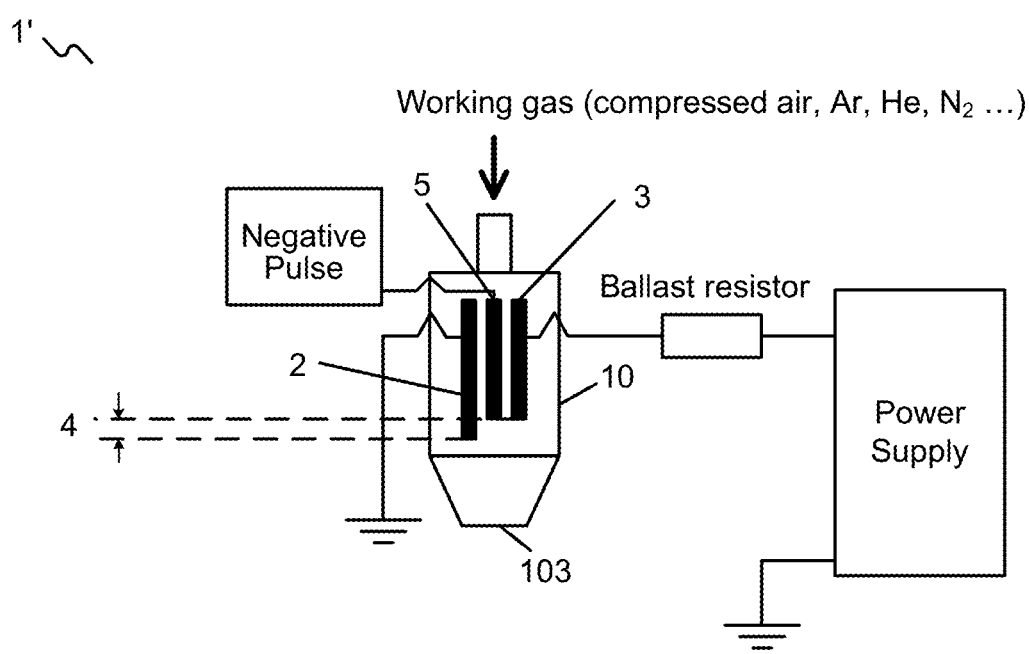
FIG. 2A is a schematic illustration of an exemplary plasma generation system with three electrodes according to an embodiment of the present disclosure.

FIG. 2A is a schematic illustration of an exemplary plasma generation system with three electrodes, according to another embodiment of the present disclosure. As shown in FIG. 2A, the plasma generation system, 1', includes three electrodes: a grounded electrode, 2, a cathode, 3, and a trigger electrode, 5, whereas the trigger electrode, 5, is arranged between the grounded electrode, 2, and the cathode, 3, at the same or similar vertical level as the cathode, 3, with a desired vertical-level difference, 4, apart from the grounded electrode, 2. Though not illustrated in the figure, the tip of trigger electrode, 5, can also assume a vertical level between those of the tip of cathode, 3, and the tip of grounded electrode, 2. The grounded electrode, 2, and the cathode, 3, are spaced apart with a distance of less than or equal to 8 mm. The trigger electrode, 5, is disposed in a middle position between the grounded electrode, 2, and the cathode, 3. At ignition, the power supply, 20, may be configured to apply a single shot of pulsed signal of 400 V to 600 V to the trigger electrode, 5. Once the plasma flame is established, the trigger electrode, 5, may return to its normal floating state. With the addition of the trigger electrode, 5, the voltage applied on the cathode, 3, can be further reduced.

Figure 2B:
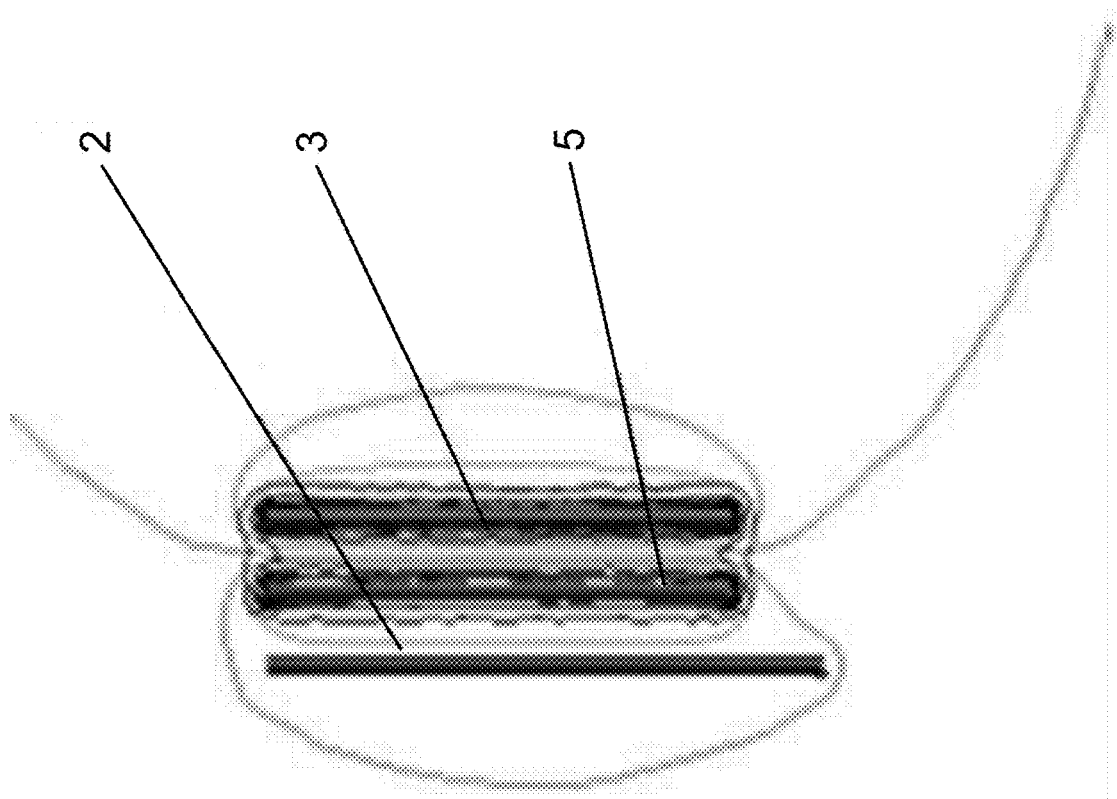
FIGS. 2B and 2C illustrate an electrostatic field distribution analyses of the exemplary system in FIG. 2A, when the trigger electrode is at on and off states.
Figure 2B:
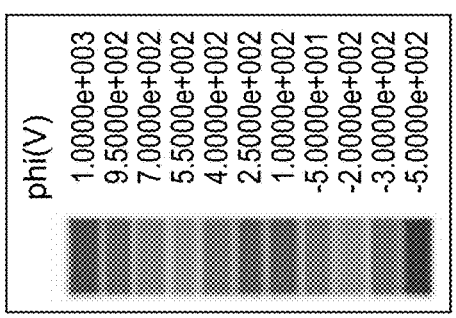
Figure 2B:
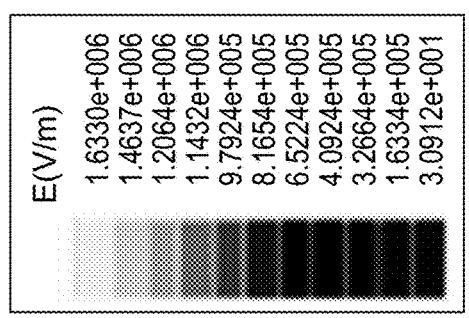
Figure 2C:
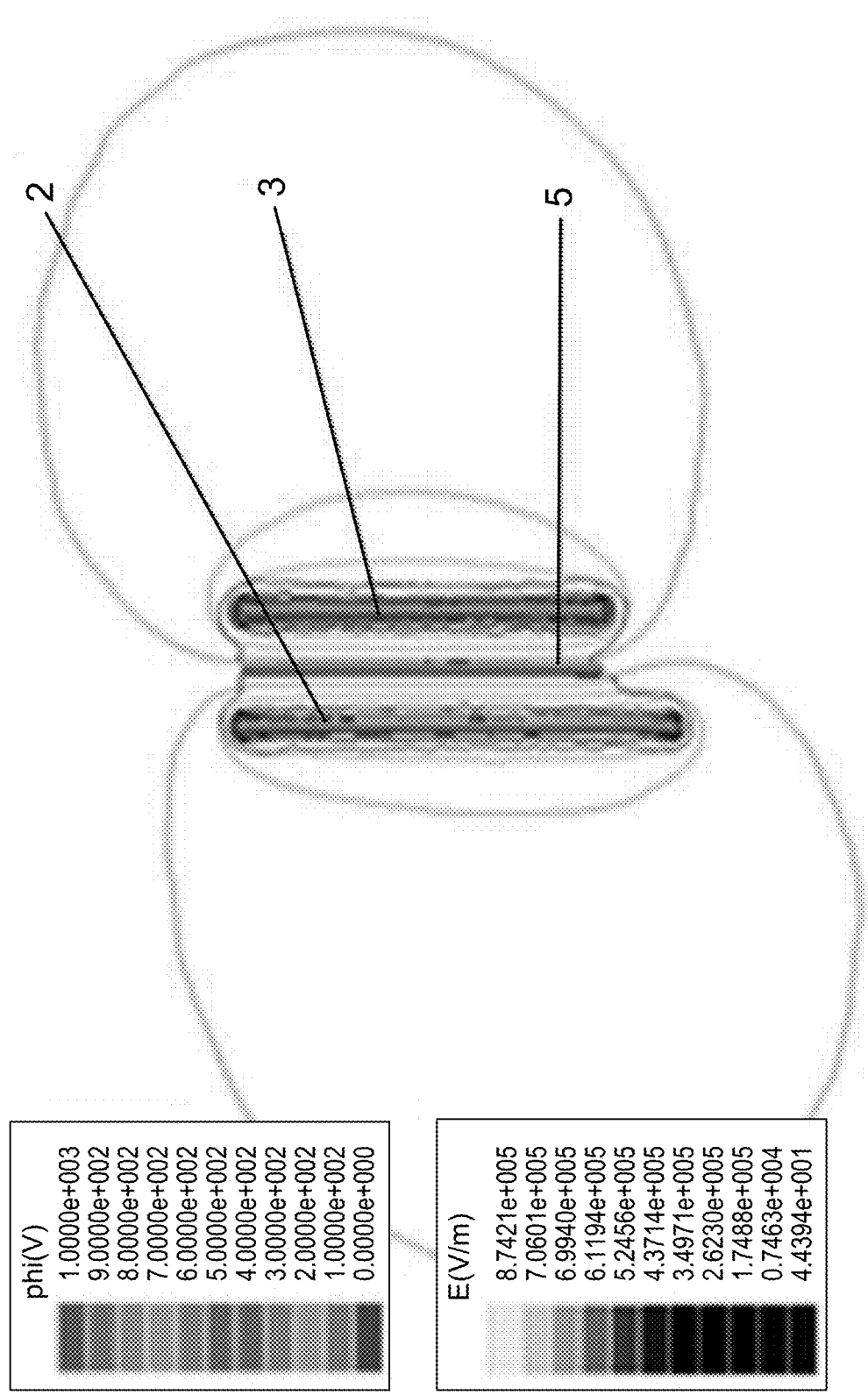

FIGS. 2B and 2C are electrostatic field distribution analysis of the three-electrode plasma source at on and off state of the trigger electrode, respectively. In this particular example, the grounded electrode, 2, cathode, 3, and trigger electrode, 5, are 30 mm, 25 mm, and 25 mm in length respectively, are made of platinum, and each has a diameter of 1 mm. The grounded electrode, 2, and the cathode, 3, are horizontally spaced apart with a distance of 8 mm. The single pulse applied to the trigger electrode, 5, is 500 V. Based on the electrostatic field analysis, the maximum field strength at an applied voltage of 1000 V to the cathode, 3, is $1.63 \times 10^6$ V/m when the trigger electrode is on, and $8.74 \times 10^5$ V/m when the trigger electrode is off. The results clearly demonstrate that the field strength is considerably increased by using the trigger electrode, indicative of easier start of plasma flame.

Figure 3A:
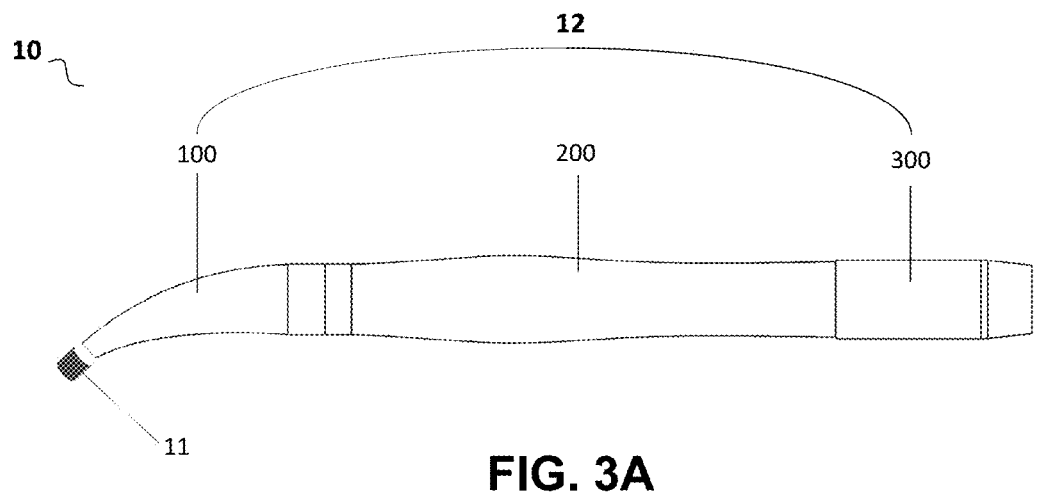
FIGS. 3A to 3C are schematic illustrations of exemplary hand-pieces, according to several embodiments of the present disclosure.
Figure 3B:
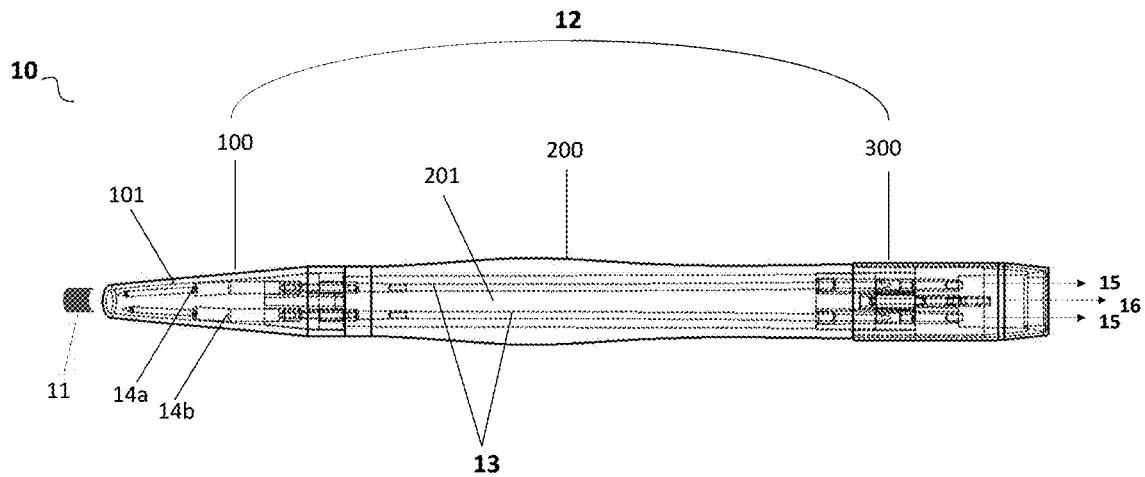
Figure 3C:
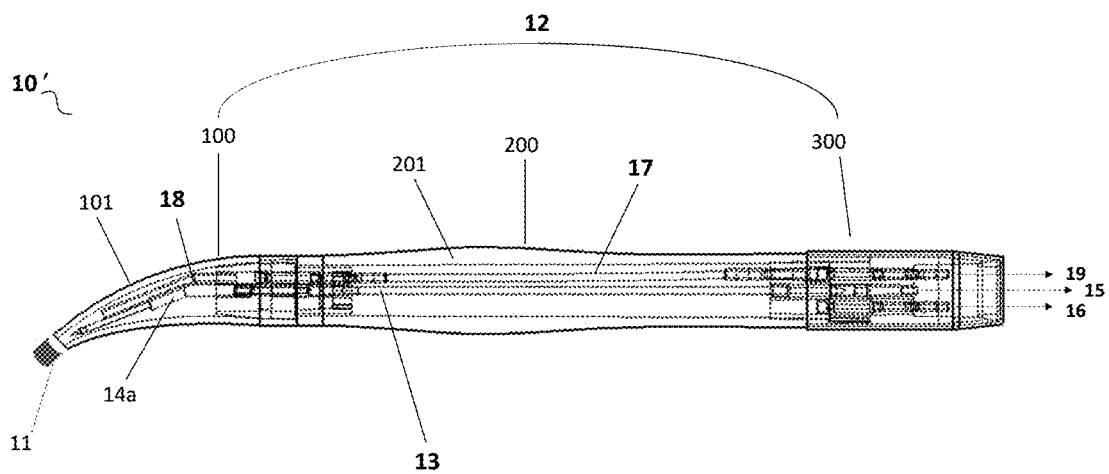

FIGS. 3A to 3C are schematic illustrations of hand-pieces according to various embodiments of the present disclosure. As shown in FIG. 3A, which is a side-view illustration of a hand-piece when assembled, the hand-piece, 10, includes a segmented housing member, 12, with three main segments, a tip member, 100, a shaft member, 200, and a tubing connection member, 300. According to one embodiment of the present disclosure, the tip member, 100, assumes a hollow conical shape, optionally bent or curved for targeted and localized delivery (especially for hard to reach areas). The shaft member, 200, assumes an elongated tubular shape, optionally curved to facilitate easy grasping or holding by a user. The tubing connection member, 300, provides easy connections to a power source and plasma gas supplies. During an application, a stable and controlled plasma flame, 11, shaped as a "brush," can be generated at an opening of the tip member, 100. In the embodiment illustrated in FIG. 3A, the hand-piece, 10, is segmented and attachable. Alternatively, in another embodiment, the hand-piece, 10, can be formed integrally as one piece.

As shown in FIG. 3B, which is a top-view transparent illustration of the hand-piece according to an embodiment (with only a plasma carrier-gas supply employed), the hand-piece, 10, further includes, in addition to the housing member, 12, a plurality of electric lines (a pair is illustrated), 13, and a plurality of electrodes 14a (ground) and 14b (cathode). The trigger electrode is not illustrated in FIG. 3B. Also as shown in FIG. 3B, the electric lines, 13, are housed in a shaft chamber, 201, of the shaft member, 200, and the electrodes, 14a/4b, are housed in in a tip chamber, 101, of the tip member, 100. After being assembled, the electrodes, 14a/4b, and their corresponding electric lines, 13, are connected to each other and to a power source, 15, and the grounded electrode, 14a, is grounded via the tubing connection member 300. Furthermore, a plasma carrier-gas supply, 16, delivers plasma carrier-gas through a carrier-gas passage unit created by aligning the shaft chamber, 201, and tip chamber, 101.

As shown in FIG. 3C, which is a side-view transparent illustration of a hand-piece according to another embodiment (with an reactive-gas supply in addition to the plasma carrier-gas supply illustrated in FIG. 3B), the hand-piece, 10', further includes, in addition to the elements included in the hand-piece illustrated in FIG. 3B, a reactive-gas passage unit created by two segments of reactive-gas tubes, 17 and 18, connected to a reactive-gas supply, 19. As also shown in FIG. 3C, the proximate reactive-gas tube, 17, is housed in the shaft chamber, 201, while the distal reactive-gas tube, 18, is housed in the tip chamber, 101, with the tip of the distal reactive-gas tube, 18, placed in near approximate with the tip of the grounded electrode, 14a. The justification for placing the distal reactive-gas tube, 18, close to the grounded electrode, 14a, and away from the cathode, 14b, is that the cathode, 14b, when connected with a power source, generates heats, and it's beneficial for positioning the reactive-gas away from the heat source. In the embodiment illustrated in FIG. 3C, the reactive-gas passage unit is formed as segmented and attachable. Alternatively, in another embodiment, the reactive-gas passage unit can be integrally formed as one piece.

Figure 4A:
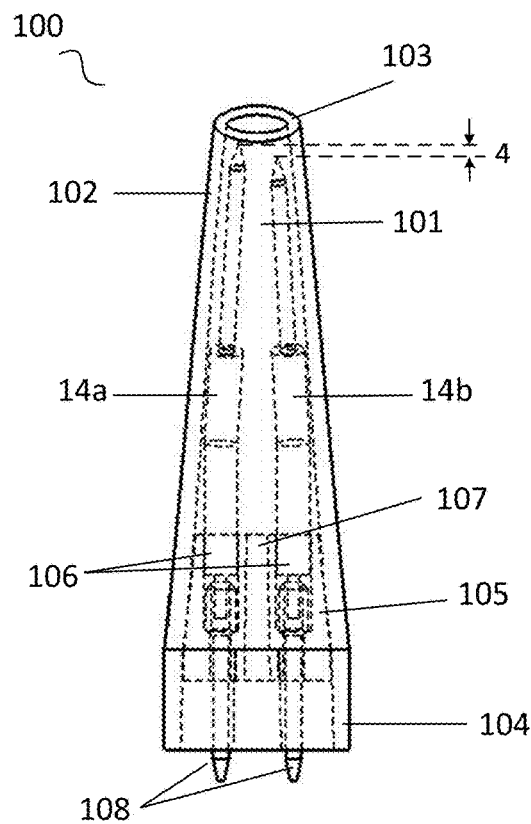
FIGS. 4A to 4F are schematic illustrations of exemplary tip members, according to several embodiments of the present disclosure.
Figure 4B:
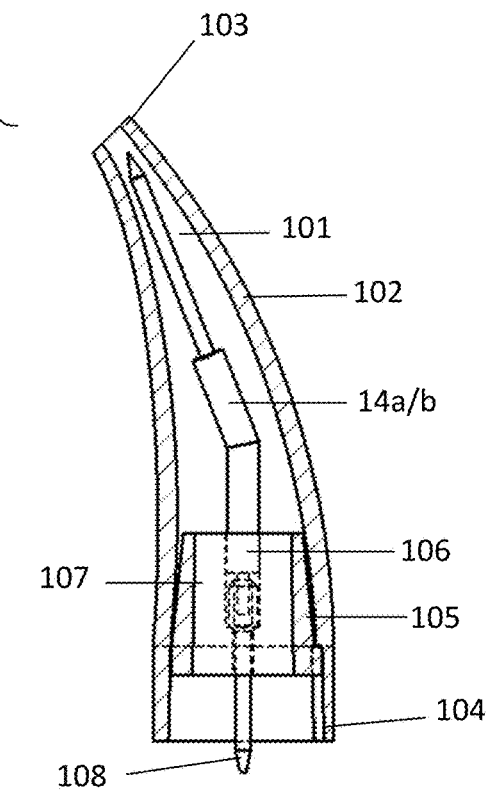
Figure 4C:
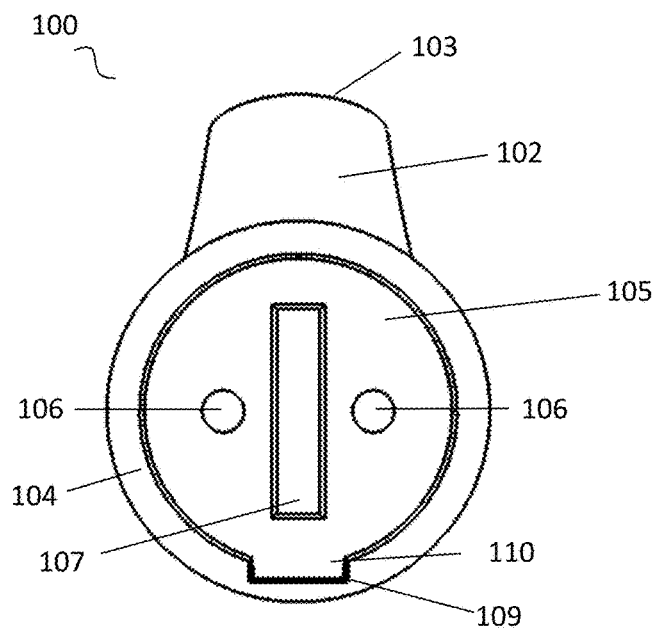
Figure 4D:
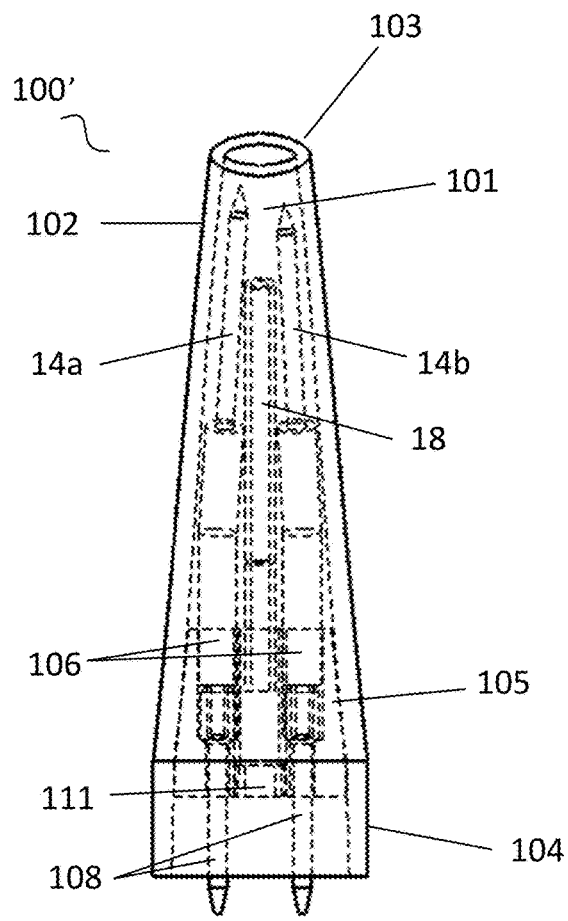
Figure 4E:
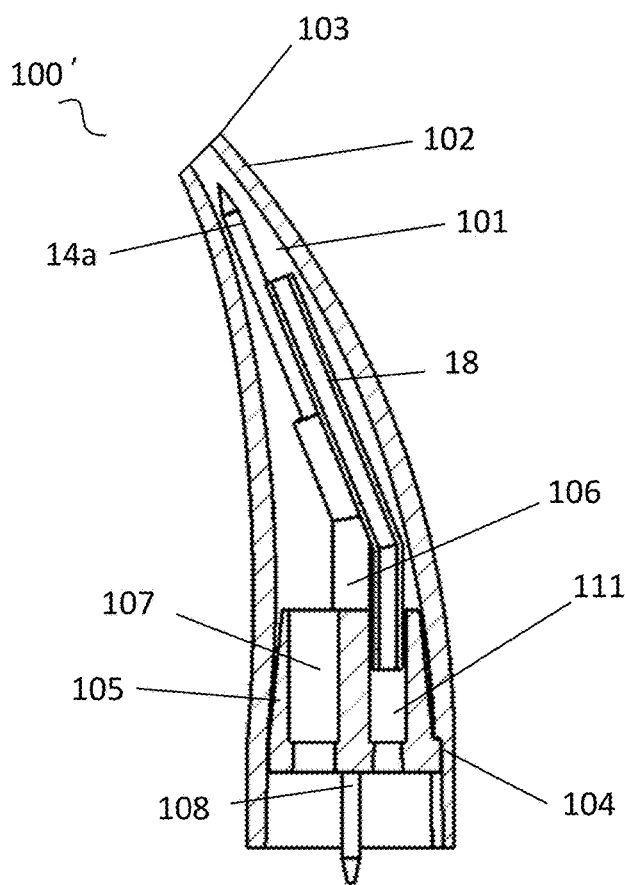
Figure 4F:
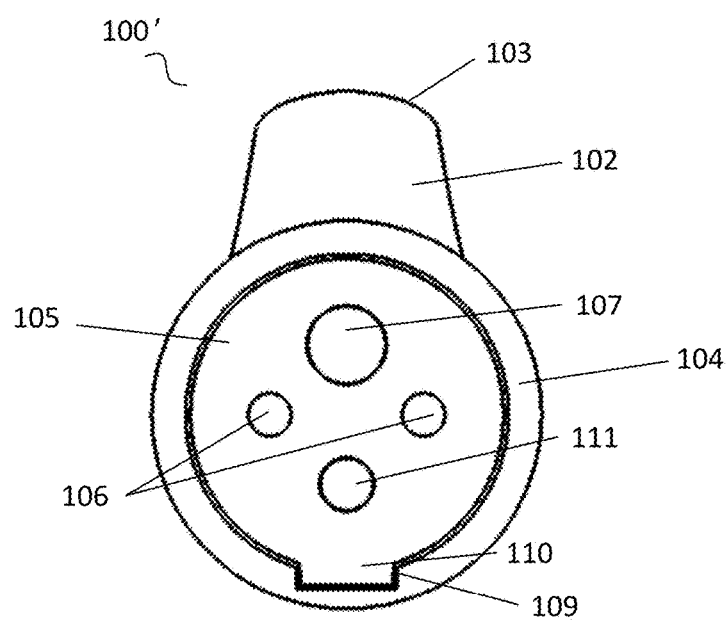

FIGS. 4A to 4F are schematic illustrations of the tip member, 100, according to various embodiments of the present disclosure. FIGS. 4A to 4C are illustrations of the tip member when only a carrier-gas supply (without reactive-gas) is employed to generate plasma flame, while FIGS. 4D to 4F are illustrations of the tip member when a reactive-gas supply and a reactive-gas passage are included. Though theoretically a reactive-gas might be mixed with the carrier-gas at the gas supply before connecting to the hand-piece, the mixed gas might not provide stable and desired plasma flame.

As shown in FIG. 4A, which is a front-view transparent illustration of an exemplary tip member, according to one embodiment of the present disclosure with only a carrier-gas supply employed, the tip member, 100, includes a tip shell, 102, in hollow conical shape forming a tip chamber, 101, with a narrow tip opening, 103, and a wide tip base end, 104, and a tip insert, 105, snugly fitted inside of the tip base end, 104. The tip insert, 105, in a conical-frustum-like shape, further includes a pair of electrode slots, 106, for attaching the electrodes, 14a/b, and a first carrier-gas opening, 107, for allowing the plasma carrier-gas to flow to the tip chamber, 101, from a shaft chamber (not shown). The tip member, 100, further includes a first pair of electric connectors, 108, respectively inserted within the pair of electrode slots, 106, for connecting the electrodes, 14a/b, to their respective electric lines. The pair of connectors, 108, may be a pair of pin contacts or any other electrically conductive units. As shown in FIG. 4B, a tip of the grounded electrode, 14a, and a tip of the cathode, 14b, are placed with a vertical-level difference, 4, in a range of approximately 1 mm to approximately 6 mm. The tip of the grounded electrode, 14a, is closer to the tip opening, 103, than the tip of the cathode, 14b. That is, a distance between the tip of the grounded electrode, 14a, and the tip opening, 103, is shorter than a distance between the tip of the cathode, 14b, and the tip opening, 103.

As shown in FIG. 4B, which is the cross-sectional side view of the tip member similar to the one illustrated in the FIG. 4A, the tip member 100 includes: a) the hollow conical tip shell, 102, optionally (and preferably) bent or curved at its narrow tip with the tip opening, 103, and straight at its tip base end, 104, to form the tip chamber, 101, and b) the tip insert, 105, fitted inside of the tip base end, 104. The tip insert, 105, has the first carrier-gas opening, 107, and the pair of electrode slots (only one shown), 106, for attachments of electrodes (only one shown), 14a/b. The tip insert, 105, further has the first pair of electric connectors, 108, such as electric contact pins, for connecting the electrodes with their respective electric lines in the shaft chamber (not shown).

As shown in FIG. 4C, which is a bottom view (from the tip base) of the tip member similar to the one illustrated in both FIG. 4A and FIG. 4B, the tip member 100, includes a tip shell, 102, having the narrow tip opening, 103, and the wide tip base end, 104, and the tip insert, 105, fitted inside of the tip base, 104. The tip insert, 105, includes the pair of electrode slots, 106, and the first carrier-gas opening, 107, which can assume various shapes including the one shown.

In the embodiment shown in FIG. 4C, the tip insert, 105, and the tip base, 104, have a first set of matching assembly-orientation-indication units, 110 and 109, respectively, to ensure easy and smooth insertion of the tip insert, 105, into the tip base, 104. The matching assembly-orientation-indication units may adopt various structures, while the pair, 110/109, shown in FIG. 4C is formed as a pair of matching slots to provide additional benefit of secure fitting between the tip insert, 105, and the tip base, 104.

As shown in FIG. 4D, which is a front-view transparent illustration of another exemplary tip member, according to one embodiment of the present disclosure with a reactive-gas passage unit, the tip member, 100', includes a) a tip shell, 102, in a hollow conical shape forming a tip chamber, 101, with a narrow tip opening, 103, and a wide tip base end, 104, and b) a tip insert, 105, in a conical-frustum-like shape, snugly fitted inside of the tip base end, 104. The tip insert, 105, further includes a pair of electrode slots, 106, for attaching the electrodes, 14a/b, a first carrier-gas opening, 107 (not shown), and a first reactive-gas slot, 111, for attaching a distal reactive-gas tube, 18, and allowing the distal reactive-gas tube, 18, to connect with a proximate reactive-gas tube (not shown). The tip member, 100', further includes a first pair of electric connectors, 108, inserted in the electrode slots, 106, for connecting the electrodes to their respective electric lines (not shown).

As shown in FIG. 4E, which is the cross-sectional side view of the tip member similar to the one illustrated in the FIG. 4D, the tip member, 100', includes a) the hollow conical shell, 102, optionally (and preferably) bent or curved at its narrow tip with the tip opening, 103, and straight at its wide tip base end, 104, to form the tip chamber, 101, and b) the tip insert, 105, fitted inside of the tip base end, 104. The tip insert, 105, in a conical-frustum-like shape, has a pair of electrode slots (only one shown), 106, for the attachments of the electrodes (only one shown), 14a/b, the first carrier-gas opening, 107, for the passage of the carrier-gas, and the first reactive-gas slot, 111, for the attachment of the reactive-gas tube, 18. The placement of the reactive-gas tube, 18, is preferred to be closer to the grounded electrode, 14a, and relatively away from the cathode, 14b. The tip member, 100', further includes the first pair of electric connectors, 108, such as electric contact pins, for connecting the electrodes with their respective electric lines (not shown).

As shown in FIG. 4F, which is a bottom view (from the tip base) of the exemplary tip member similar to the one illustrated in both FIG. 4D and FIG. 4E, the tip member, 100', includes the tip shell, 102, having the narrow tip opening, 103, and the wide tip base end, 104, and the tip insert, 105, fitted inside of the tip base, 104. The tip insert, 105, has the pair of electrode slots, 106, the first carrier-gas opening, 107, which can assume various shapes other than the one shown, and the first reactive-gas slot, 111. In the embodiment shown in FIG. 4F, the tip insert, 105, and the tip base, 104, are further equipped with matching assembly-orientation-indication units, 110 and 109, respectively, to ensure easy and smooth insertion of the tip insert, 105, into the tip base, 104. The matching indication units may adopt various structures, while the pair, 110/109, shown in FIG. 4F is formed as a pair of matching slots to provide additional benefit of secure fitting between the tip insert, 105, and the tip base, 104.

Figure 5A:
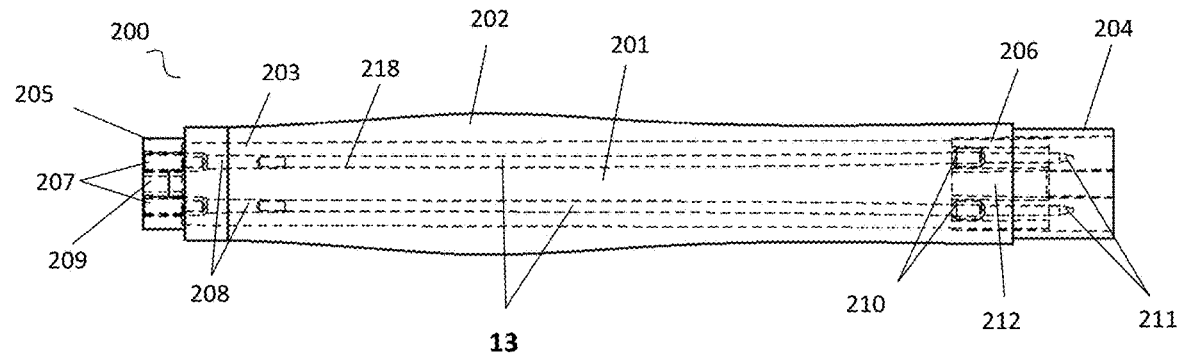
FIG. 5A to 5I are various schematic illustrations of exemplary shaft members, according to several embodiments of the present disclosure.
Figure 5B:
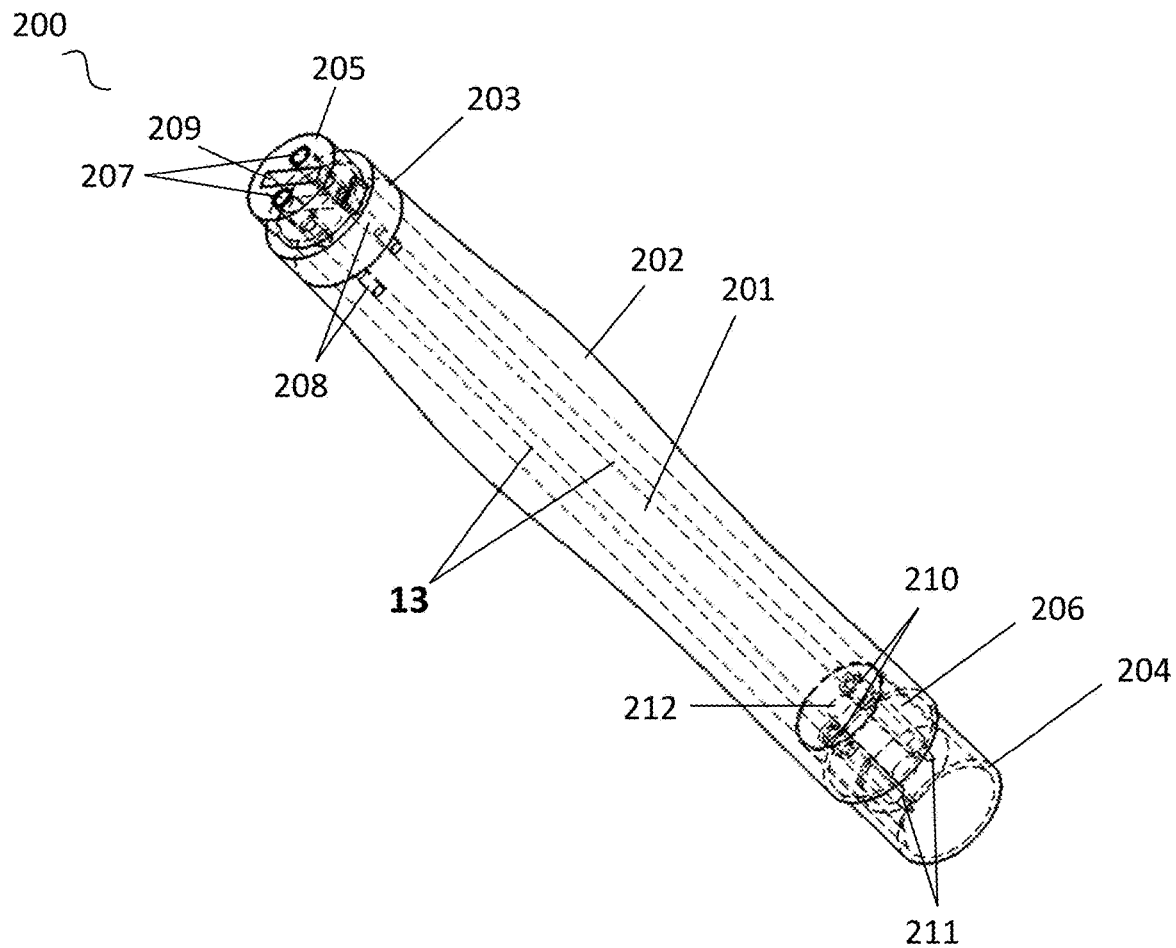
Figure 5C:
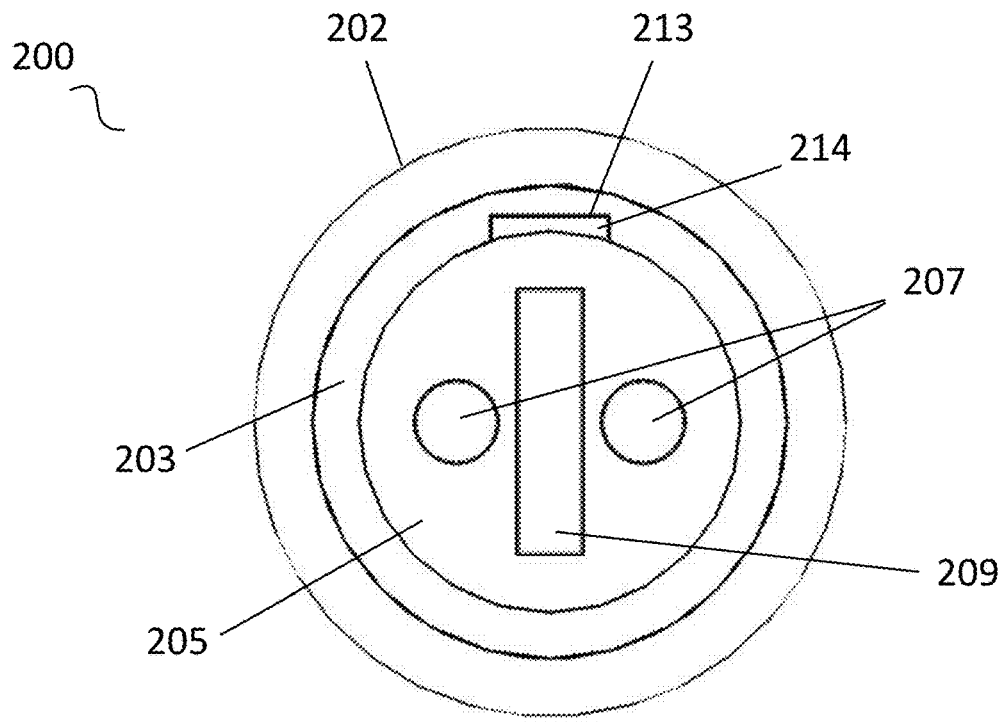
Figure 5D:
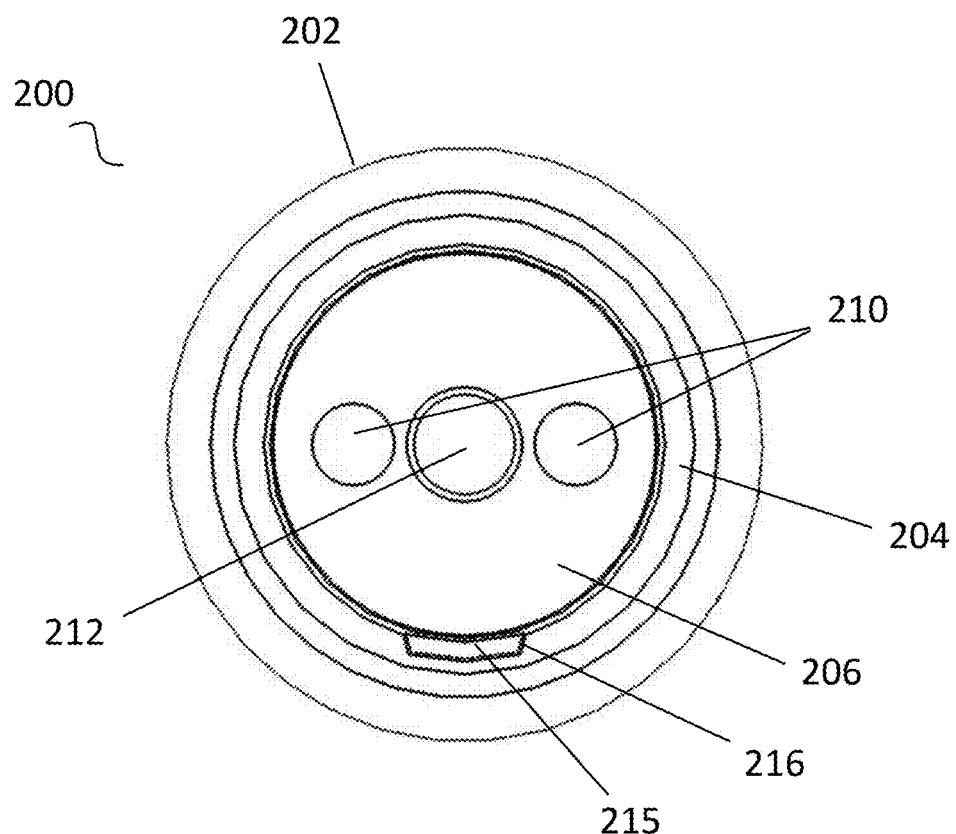
Figure 5E:
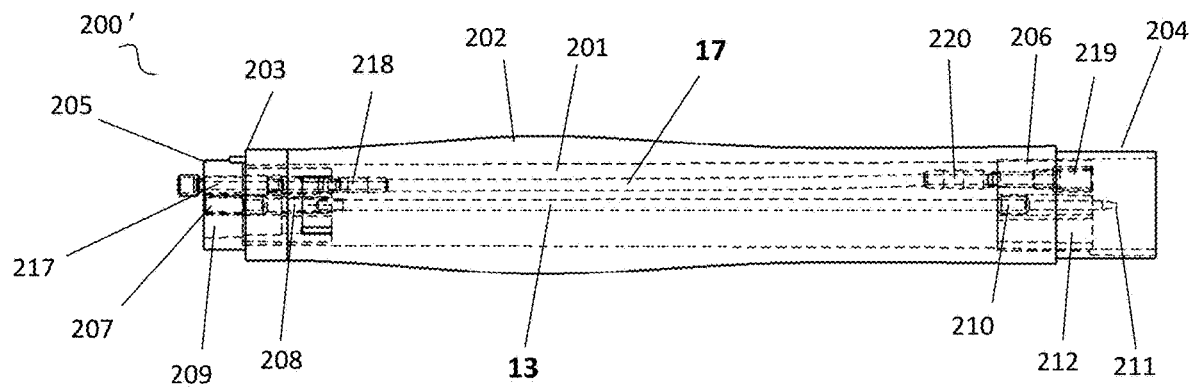
Figure 5F:
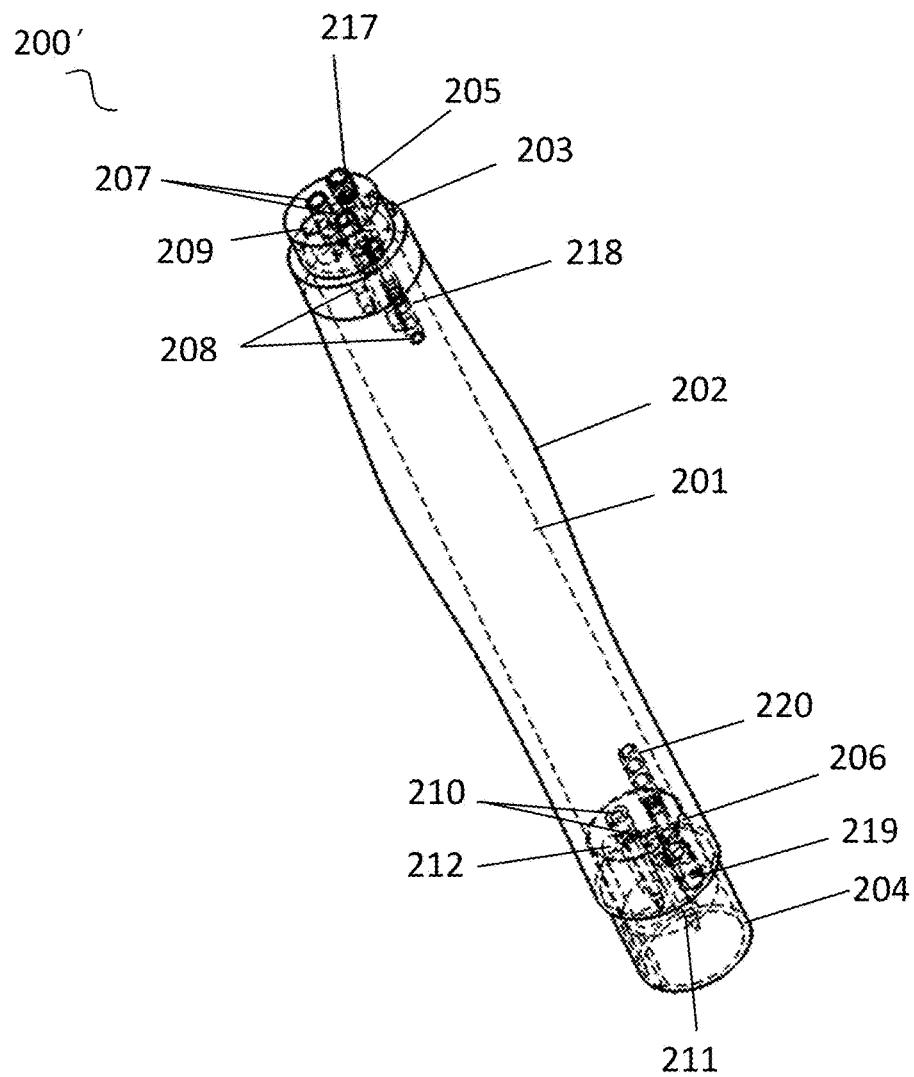
Figure 5G:
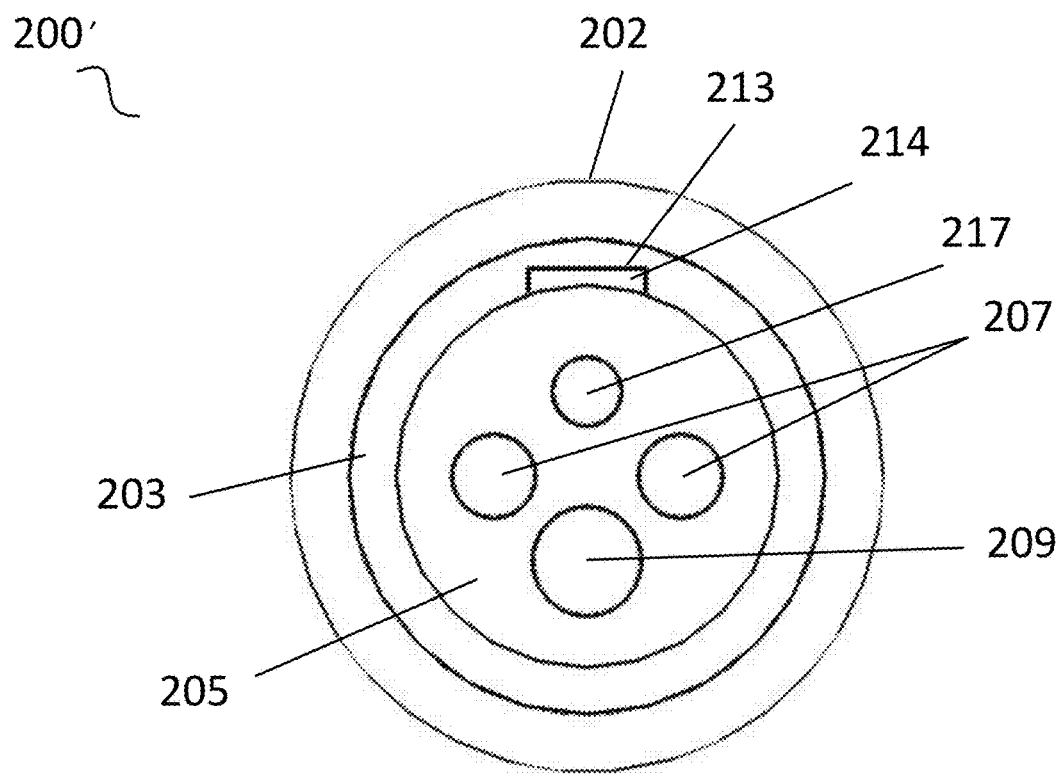
Figure 5H:
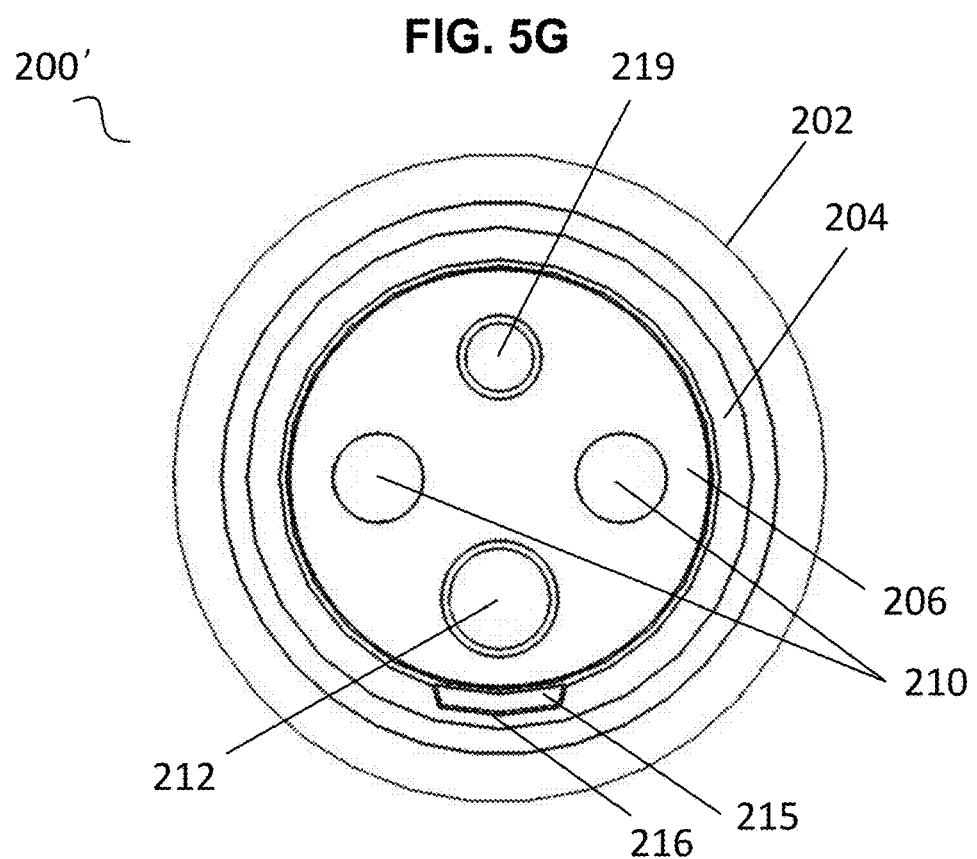
Figure 5I:
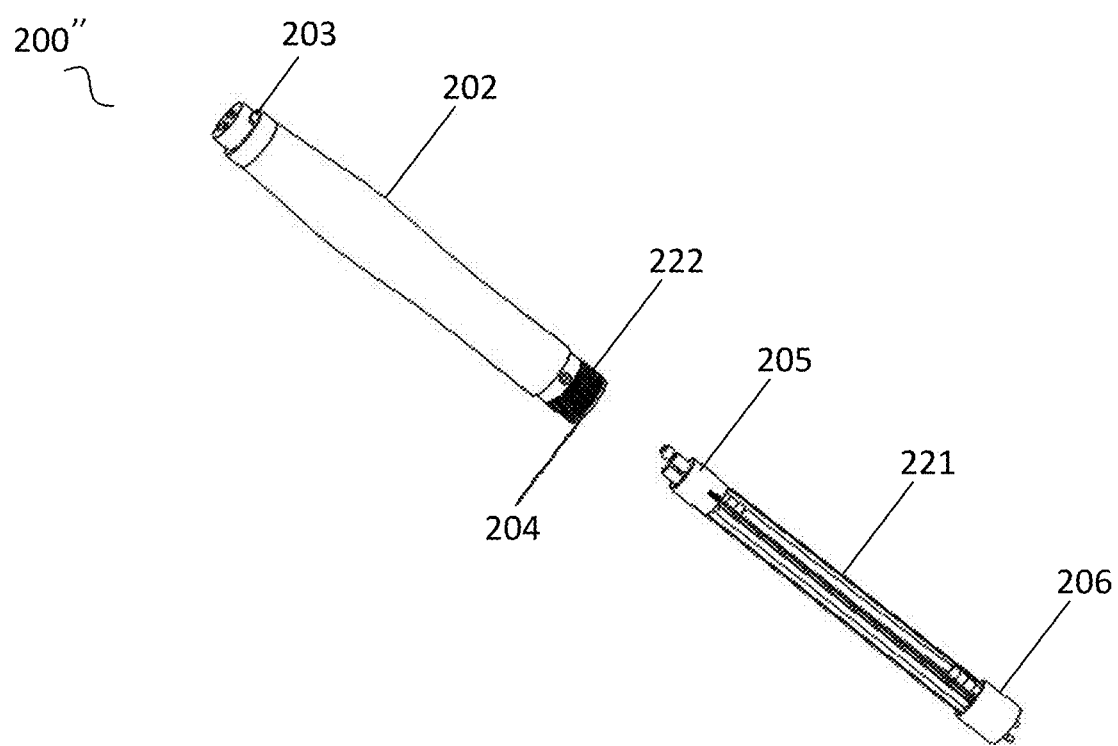

FIG. 5A to 5I are various schematic illustrations of the shaft member according to several exemplary embodiments. FIGS. 5A to 5D are schematic illustrations of an exemplary shaft member without a reactive-gas passage unit. FIGS. 5E to 5H are schematic illustrations of an exemplary shaft member with a reactive-gas passage unit. FIG. 5I is a schematic illustration of an exemplary shaft member with an optional partition unit.

As shown in FIG. 5A, which is a cross-sectional side view of an exemplary shaft member without a reactive-gas passage unit, the shaft member, 200, includes a) a shaft chamber shell, 202, in an elongated tubular shape, forming a shaft chamber, 201, with a shaft-tip end, 203, to be attached to the tip member, 100 (not shown, described above), and a shaft-connector end, 204, to be attached to the tubing connection member, 300 (not shown, described below), b) a shaft-tip insert, 205, fitted at the shaft-tip end, 203, and c) a shaft-connector insert, 206, fitted inside of the shaft-connector end, 204. The shaft chamber shell, 202, may be ergonomically modified for better gripping and handling by a user. The shaft-tip insert, 205, in a cylindrical disk shape, further includes a first pair of electric slots, 207, with a second pair of electric connectors, 208, inserted there within, for the attachments of the electric lines, 13, and a second carrier-gas opening, 209, matching the first carrier-gas opening, 107, on the tip insert, 105 (not shown, described above), to facilitate the carrier-gas passage. The shaft-tip insert, 205, may be integrally formed with the shaft chamber shell, 202. Alternatively, the shaft-tip insert, 205, may be formed separately from the shaft chamber shell, 200, and may be attached to the shaft chamber shell, 200, when the hand-piece, 10, is assembled. The shaft-connector insert, 206, further includes a second pair of electric slots, 210, with a third pair of electric connectors, 211, inserted therein, and a third carrier-gas opening, 212. As shown in FIG. 5A, the pair of electric lines, 13, is housed in the shaft chamber, 201, connected to the electric connectors, 208/211, at each end, to facilitate the electronic connections between the power source and the electrodes.

A shown in FIG. 5B, which is a 3-D transparent illustration of the exemplary shaft member similar to the one illustrated in FIG. 5A, the shaft member 200, includes the modified tubular shaft shell, 202, forming the shaft chamber, 201, with the shaft-tip end, 203, and the shaft-connector end, 204, the shaft-tip insert, 205, fitted at the shaft-tip end, 203, and the shaft-connector insert, 206, fitted inside of the shaft-connector end, 204. The shaft-tip insert, 205, includes the first pair of electric slots, 207, with the second pair of electric connectors, 208, inserted therein, and the second carrier-gas opening, 209. The shaft-connector insert, 206, includes the second pair of electric slots, 210, with the third pair of electric connectors, 211, inserted there within, and the third carrier-gas opening 212. As also shown in FIG. 5B, the electric slots, 207/210, are so aligned to ensure that the pair of electric lines, 13, housed in the shaft chamber, 201, is connected to the electric connectors, 208/211, at each end, while maintaining the desired separation between the electric lines to avoid short circuit. Optionally, a partition unit (described below and illustrated in FIG. 5I) may be employed to further isolate the electric lines to prevent short circuit.

As shown in FIG. 5C, which is a top view of the exemplary shaft member similar to the one illustrated in both FIGS. 5A and 5B, the shaft member, 200, includes the shaft shell, 202, with the shaft-tip end, 203, and the shaft-tip insert, 205, fitted at the shaft-tip end, 203. The shaft-tip insert, 205, has the first pair of electric slots, 207, and the second carrier-gas opening, 209. The second carrier-gas opening, 209, as long as matching with the first carrier-gas opening, 107 (not shown, described above), may assume various shapes including the one shown. Furthermore, the shaft-tip insert, 205, and the shaft-tip end, 203, may optionally be equipped with a second set of matching assembly-orientation-indication units, 214 and 213, respectively, to ensure easy and smooth insertion of the shaft-tip insert, 205, at the shaft-tip end, 203. The matching indication units may adopt various structures, while the pair, 214/213, shown in FIG. 5C is formed as a pair of matching slots to provide additional benefit of secure fitting between the shaft-tip insert, 205, and the shaft-tip end, 203.

As shown in FIG. 5D, which is a bottom view of the exemplary shaft member similar to the one illustrated in both FIGS. 5A and 5B, the shaft member, 200, includes the shaft shell, 202, with the shaft-connector end, 204, and the shaft-connector insert, 206, fitted inside of the shaft-connector end, 204. The shaft-connector insert, 206, has the second pair of electric slots, 210, and a third carrier-gas opening, 212. The shaft-connector insert, 206, and the shaft-connector end, 204, may optionally be equipped with a third set of matching assembly-orientation-indication units, 215 and 216, respectively, to ensure easy and smooth insertion of the shaft-connector insert, 206, into the shaft-connector end, 204. The matching indication units may adopt various structures, while the pair, 215/216, shown in FIG. 5D is a pair of matching slots that provide an additional benefit of securely fitting between the shaft-connector insert, 206, and the shaft-connector end, 204.

As shown in FIG. 5E, which is a transparent side view of another exemplary shaft member with an reactive-gas passage unit, the shaft member, 200', includes a) a shaft chamber shell, 202, in an elongated tubular shape (optionally ergonomically modified for better gripping and handling by a user), forming a shaft chamber, 201, with a shaft-tip end, 203, to be attached to the tip member, 100 (not shown, described above), and a shaft-connector end, 204, to be attached to the tubing connection member, 300 (not shown, described below), b) a shaft-tip insert, 205, fitted at the shaft-tip end, 203, and c) a shaft-connector insert, 206, fitted inside of the shaft-connector end, 204. The shaft-tip insert, 205, further includes i) a first pair of electric slots (only one shown), 207, with a second pair of electric connectors (only one shown), 208, inserted therein, ii) a second carrier-gas opening, 209, and iii) a second reactive-gas slot, 217, with a first reactive-gas fitting unit, 218, inserted therein. The shaft-connector insert, 206, further includes i) a second pair of electric slots (only one shown), 210, with a third pair of electric connectors (only one shown), 211, inserted there within, ii) a third carrier-gas opening, 212, and iii) a third reactive-gas slot, 219, with a second reactive-gas fitting unit, 220, inserted therein. As shown in FIG. 5E, the pair of electric lines (only one shown), 13, is housed in the shaft chamber, 201, connected to the electric connectors, 208/211, at each end, and a proximate reactive-gas tube, 17, is also housed in the shaft chamber, 201, and connected to the reactive-gas fitting units, 218/220, at each end.

A shown in FIG. 5F, which is a 3-D transparent illustration of the exemplary shaft member similar to the one illustrated in FIG. 5E, the shaft member, 200', includes the modified tubular shaft shell, 202, forming the shaft chamber, 201, with the shaft-tip end, 203, and the shaft-connector end, 204, the shaft-tip insert, 205, at the shaft-tip end, 203, and the shaft-connector insert, 206, at the shaft-connector end, 204. The shaft-tip insert, 205, includes the first pair of electric slots, 207, with the second pair of electric connectors, 208, inserted therein, the second carrier-gas opening, 209, and the second reactive-gas slot, 217, with the first reactive-gas fitting unit, 218, inserted therein. The shaft-connector insert, 206, includes the second pair of electric slots, 210, with the third pair of electric connectors, 211, inserted therein, the third carrier-gas opening, 212, and the third reactive-gas slot, 219, with the second reactive-gas fitting unit, 220, inserted therewithin. As also shown in FIG. 5F, the reactive-gas slots, 217/219, are so aligned to ensure that the proximate reactive-gas tube, 17, is connected to the reactive-gas fitting units, 218/220, at each end, while the electric slots, 207/210, are so aligned to ensure that the pair of electric lines, 13, is connecting to the electric connectors, 208/211, at each end, and maintaining the desired separation between the electric lines to avoid short circuit. Optionally, a partition unit (described below and illustrated in FIG. 5I) may be employed to further isolate the electric lines to prevent short circuit.

As shown in FIG. 5G, which is a top view of the exemplary shaft member similar to the one illustrated in both FIGS. 5E and 5F, the shaft member, 200', includes the shaft shell, 202, with the shaft-tip end, 203, and the shaft-tip insert, 205, fitted at the shaft-tip end, 203. The shaft-tip insert, 205, has the first pair of electric slots, 207, the second carrier-gas opening, 209, and the second reactive-gas slot, 217. Again, the second carrier-gas opening, 209, as long as matching with the first carrier-gas opening, 107 (not shown, described above), may assume various shapes including the one shown.

Furthermore, the shaft-tip insert, 205, and the shaft-tip end, 203, may be optionally equipped with the second set of matching assembly-orientation-indication units, 214 and 213, respectively, to ensure easy and smooth insertion of the shaft-tip insert, 205, at the shaft-tip end, 203. The matching indication units may adopt various structures, while the pair, 213/214, shown in FIG. 5G is formed as a pair of matching slots to provide additional benefit of secure fitting between the shaft-tip insert, 205, and the shaft-tip end, 203.

As shown in FIG. 5H, which is a bottom view of the exemplary shaft member similar to the one illustrated in both FIGS. 5E and 5F, the shaft member, 200', includes the shaft shell, 202, with the shaft-connector end, 204, and the shaft-connector insert, 206, fitted inside of the shaft-connector end, 204. The shaft-connector insert, 206, has the second pair of electric slots, 210, the third carrier-gas opening, 212, and the third reactive-gas slot, 219. Again, the shaft-connector insert, 206, and the shaft-connector end, 204, may be optionally equipped with the third set of matching assembly-orientation-indication units, 215 and 216, respectively, to ensure easy and smooth insertion of the shaft-connector insert, 206, into the shaft-connector end, 204. The matching indication units may adopt various structures, while the pair, 215/216, shown in FIG. 5D is a pair of matching slots that provide an additional benefit of securely fitting between the shaft-connector insert, 206, and the shaft-connector end, 204.

As shown in FIG. 5I, which is an exploded 3-D view of yet another exemplary shaft member with an optional partition unit according to an embodiment of the present disclosure, the shaft member, 200", further includes a partition unit, 221, installed between the shaft-tip insert, 205, and the shaft-connector insert, 206. The partition unit, 221, can assume various shapes to function as an insulator to prevent short circuit of the electric lines, and as a support to stabilize the shaft-tip insert, 205, inserted at the shaft-tip end, 203, and the shaft-connector insert, 206, inserted at the shaft-connector end, 204. Furthermore, optionally the external surface of the shaft-connector end, 204, includes an array of screw thread, 222, which matches screw threads on an internal surface of an element of the tubing connection member (described below) to provide secure attachment between the shaft member and the tubing connection member.

Figure 6A:
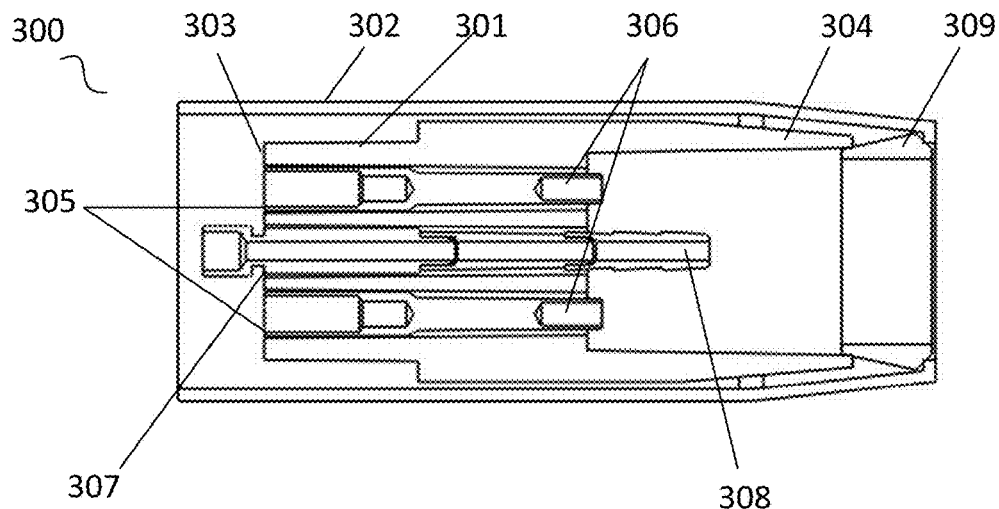
FIGS. 6A to 6F are the schematic illustrations of exemplary tubing connection members, according to several embodiments of the present disclosure.
Figure 6B:
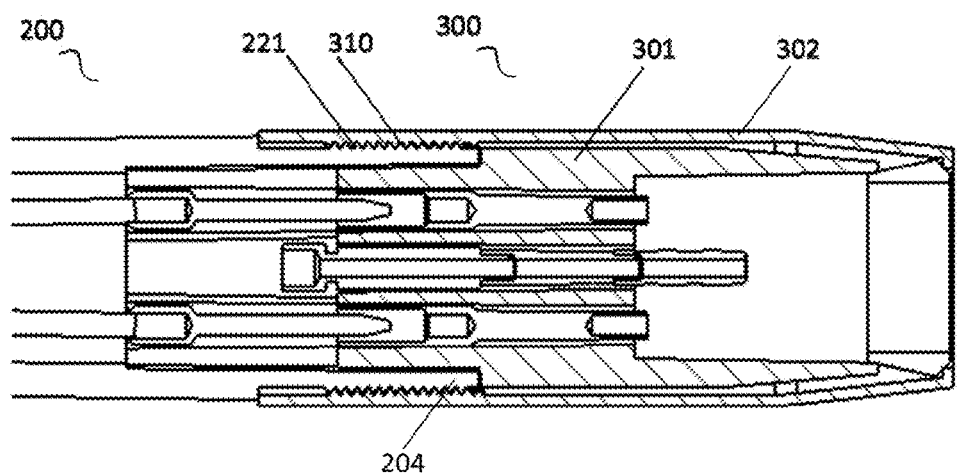
Figure 6C:
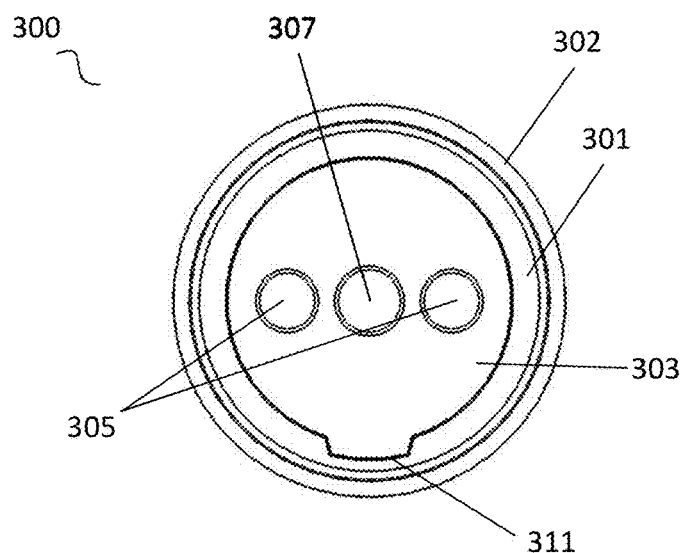
Figure 6D:
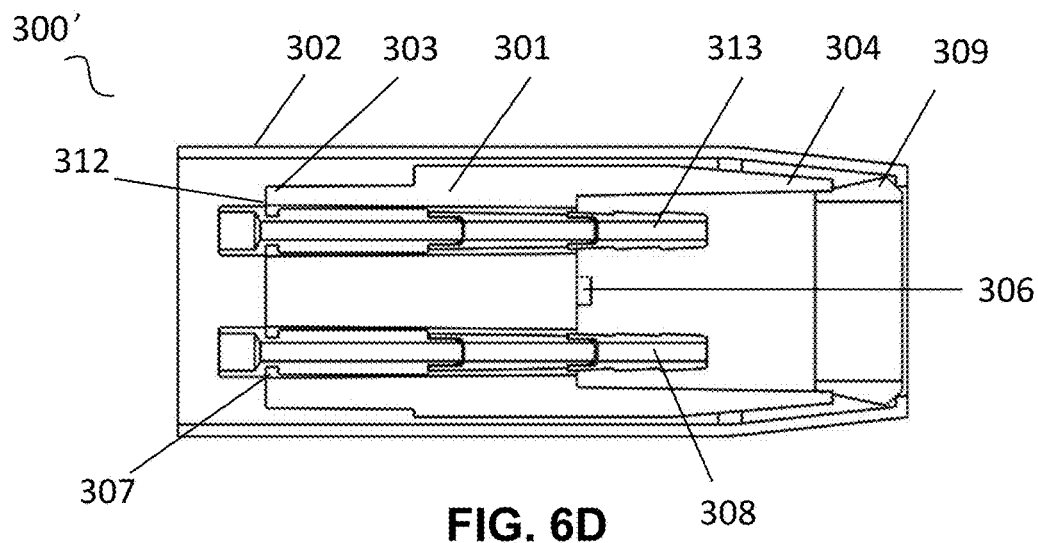
Figure 6E:
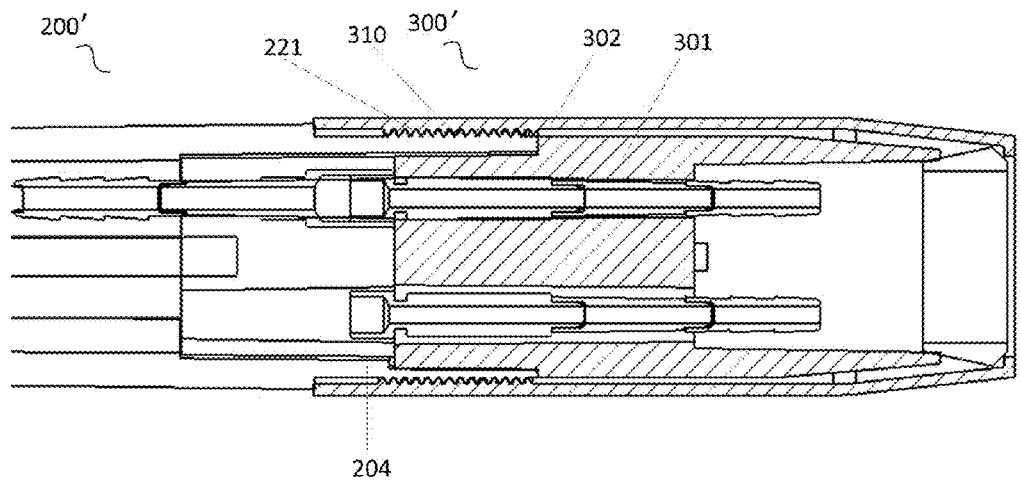
Figure 6F:
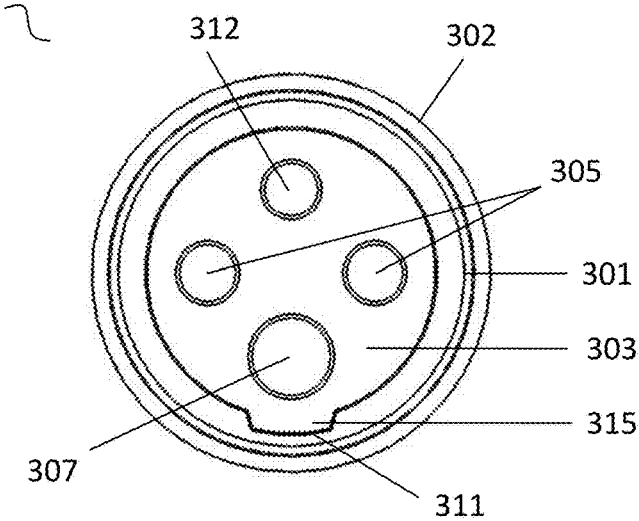

FIGS. 6A to 6F are the schematic illustrations of the tubing connection member, according to several disclosed embodiments. FIGS. 6A to 6C are schematic illustrations of the tubing connection member when a reactive-gas is not employed, and FIGS. 6D to 6F are schematic illustrations of the tubing connection member when a reactive-gas is employed.

As shown in FIG. 6A, which is a cross-section side view of an exemplary tubing connection member according to one embodiment without reactive-gas passage unit, the tubing connection member, 300, includes a source connector, 301, and a connector collet or sleeve, 302. The connector collet, 302, is in an elongated tubular shape and can slide over the source connector, 301, and partially over the shaft-connector end to facilitate a secure attachment between the tubing connection member and the shaft member. The source connector, 301, may be in a modified cylindrical shape having an adaptor end, 303, and a tubing end, 304, wherein the adaptor end, 303, is in a cylindrical disk shape with a reduced-diameter to be inserted into the shaft-connector end of the shaft member during assembly, and the tubing end, 304, is in a tapered tubular shape to be connected with a source tubing. The source connector, 301, further includes, at the adaptor end, 303, a third pair of electric slots, 305, and a fourth carrier-gas opening, 307, and at the tubing end, 304, optionally a compression ring, 309, providing enhanced fitting when connected with the source tubing. The third pair of electric slots, 305, further includes a fourth pair of electric connectors, 306, inserted therein, while the fourth carrier-gas opening, 307, includes a carrier-gas fitting unit, 308.

As shown in FIG. 6B, which is another cross-sectional side view of the exemplary tubing connection member, similar to the embodiment illustrated in FIG. 6A, assembled with the shaft member, 200, the tubing connection member (the shaded member), 300, further includes an array of screw threads, 310, on part of an internal surface of the connector collet, 302. As also shown in FIG. 6B, the screw threads, 310, on the internal surface of the connector collet, 302, further matches the screw threads, 221, on the external surface of the shaft-connector end, 204, of the shaft member, 200. After being assembled, the connector collet, 302, slides over the source connector, 301, and fastens on the shaft-connector end, 204, to facilitate a secure attachment between the source connector, 301, and the shaft member, 200, and to ensure secure connections between the two sets of electric connectors and between the sets of gas fitting units.

As shown in FIG. 6C, which is a top view of the exemplary tubing connection member similar to the embodiment illustrated in both FIGS. 6A and 6B, the tubing connection member, 300, includes the connector collet, 302, and the source connector, 301. The adaptor end, 303, of the source connector, 301, has the third pair of electric slots, 305, and the fourth carrier-gas opening, 307. The adaptor end, 303, may be optionally equipped with an assembly-orientation-indication unit, 311, matching the assembly-orientation-indication unit on the shaft-connector end (not shown), 204, to provide additional benefit of secure fitting between the source connector, 301, and the shaft-connector end, 204.

As shown in FIG. 6D, which is a cross-section side view of another exemplary tubing connection member according to one embodiment with a reactive-gas passage unit, the tubing connection member, 300', includes a source connector, 301, and a connector collet, 302. The connector collet, 302, is in an elongated tubular shape and can slide over the source connector, 301, and partially over the shaft-connector end of the shaft member to facilitate a secure attachment between the tubing connection member and the shaft member during assembly. The source connector, 301, with its adaptor end, 303, and its tubing end, 304, further includes a third pair of electric slots (not shown in the current view), 305, a fourth carrier-gas opening, 307, and a fourth reactive-gas slot, 312, at the adaptor end, 303, and optionally a compression ring, 309, at the tubing end, 304. Like the embodiment illustrated in FIGS. 6A to 6C, the third pair of electric slots (not shown), 305, also includes a fourth pair of electric connectors (only the tip of one shown), 306, inserted therein. A carrier-gas fitting unit, 308, is inserted within the fourth carrier-gas opening, 307, and a reactive-gas fitting unit, 313, is inserted within the fourth reactive-gas slots, 312.

As shown in FIG. 6E, which is another cross-sectional side view of the exemplary tubing connection member, similar to the embodiment illustrated in FIG. 6D, assembled with the shaft member, the tubing connection member (the shaded member), 300', further includes the array of screw threads, 310, on part of the internal surface of the connector collet, 302. The screw threads, 310, on the internal surface of the connector collet, 302, matches the screw threads, 221, on the external surface of the shaft-connector end, 204, of the shaft member, 200'. After being assembled, the connector collet, 302, slides over the source connector, 301, and fastens upon the shaft-connector end, 204, to facilitate a secure attachment between the source connector, 301, and the shaft member, 200', and to ensure secure connections between the two sets of electric connectors and between the sets of gas fitting units.

As shown in FIG. 6F, which is a top view of the exemplary tubing connection member similar to the embodiment illustrated in both FIGS. 6D and 6E, the tubing connection member, 300', includes the connector collet, 302, and the source connector, 301. The adaptor end, 303, of the source connector, 301, has the third pair of electric slots, 305, the fourth carrier-gas opening, 307, and the fourth reactive-gas slot, 312. Again, the adaptor end, 303, may be optionally equipped with the assembly-orientation-indication unit, 311, matching the assembly-orientation-indication unit on the shaft-connector end, 204, to provide additional benefit of secure fitting between the source connector, 301, and the shaft-connector end, 204.

Figure 7:
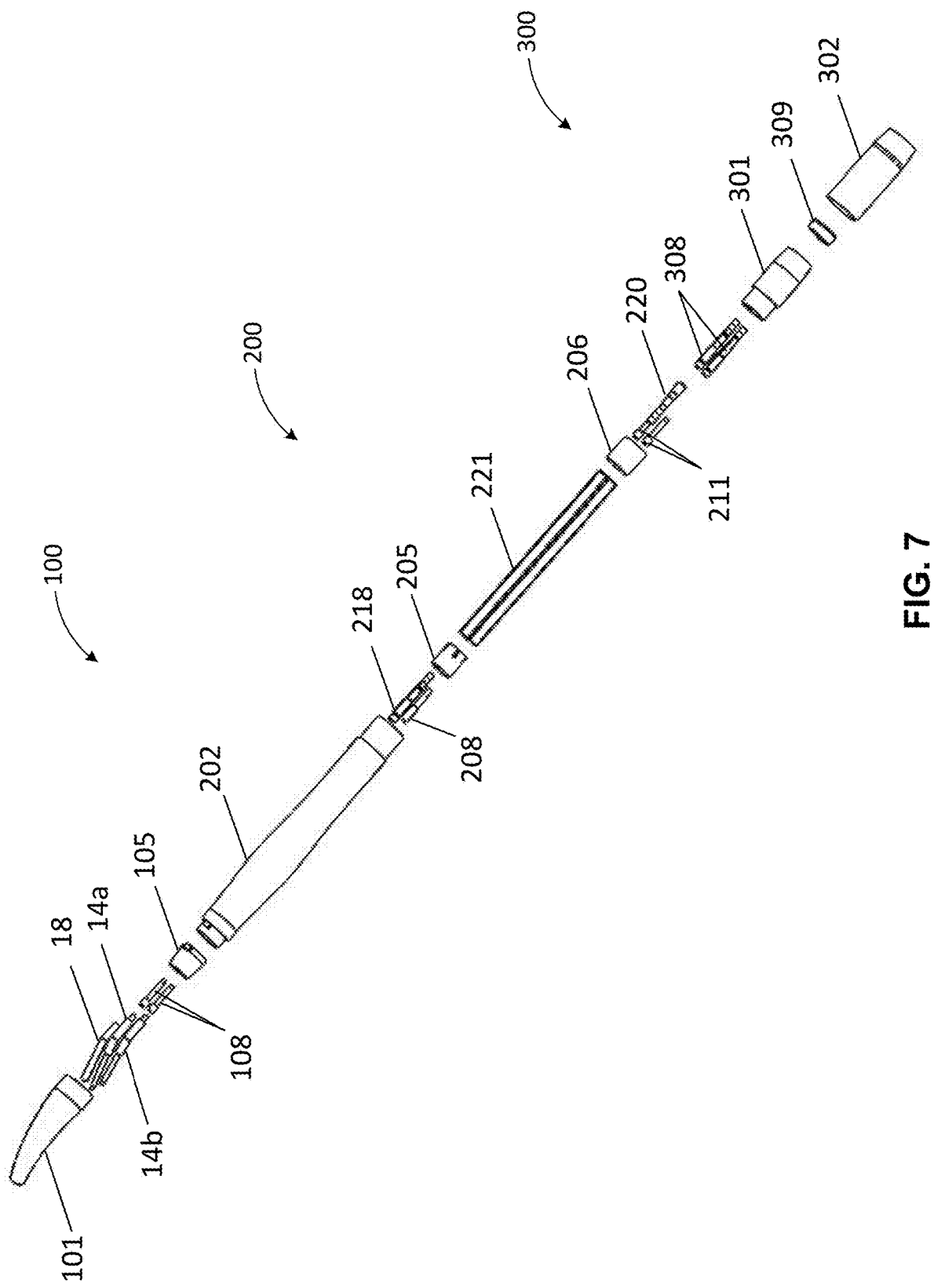
FIG. 7 is an exploded illustration of an exemplary hand-piece with a partition unit, according to an embodiment of the present disclosure.

FIG. 7 is an exploded illustration of an exemplary hand-piece according to an embodiment of the present disclosure in which the hand-piece, 10, includes the tip member, 100, a shaft member, 200, and a tubing connection member, 300. The tip member, 100, includes a tip chamber, 101, and a tip insert, 105. The tip member, 100, also includes a first pair of electric connectors, 108, for connecting electrodes, 14a/b, to their respective electric lines. A distal reactive-gas tube, 18, is housed in the tip chamber, 101. The shaft member, 200, includes a shaft chamber shell, 202, a shaft-tip insert, 205, and a shaft-connector insert, 206. The shaft-tip insert, 205, includes a first pair of electric slots (not shown) with a second pair of electric connectors, 208, inserted therein, and a second reactive-gas slot (not shown) with a first reactive-gas fitting unit, 218, inserted therein. The shaft-connector insert, 206, includes a second pair of electric slots (not shown) with a third pair of electric connectors, 211, inserted there within, and a third reactive-gas slot (not shown) with a second reactive-gas fitting unit, 220, inserted therein. The shaft member, 200, further includes a partition unit, 221, installed between the shaft-tip insert, 205, and the shaft-connector insert, 206. The tubing connection member, 300, includes a source connector, 301, and a connector collet, 302. The source connector, 301, includes a compression ring, 309, at its tubing end, and a carrier-gas fitting unit, 308.

Figure 8:
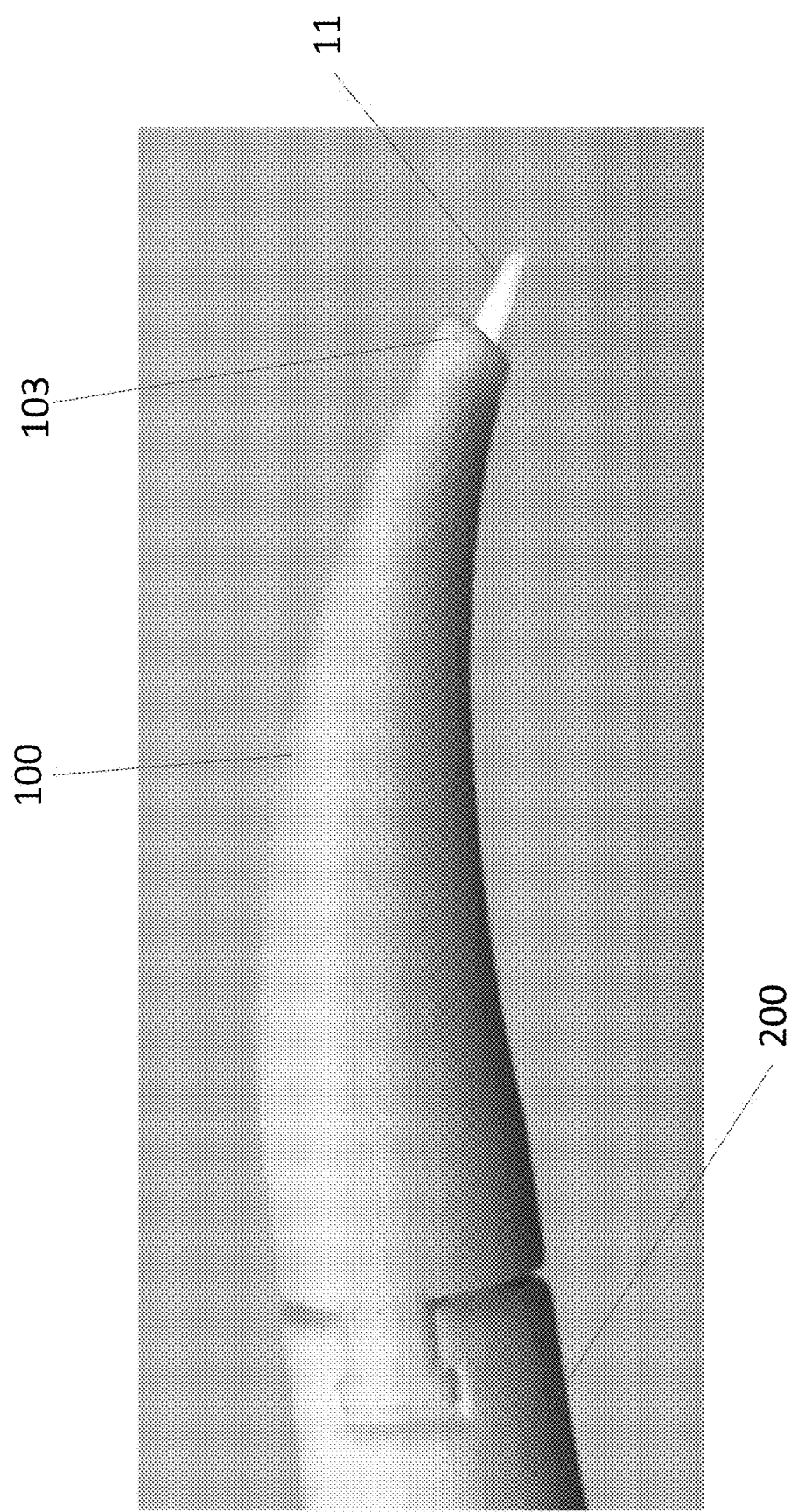
FIG. 8 is a picture illustration of a typical plasma flame generated by an exemplary inventive hand-piece.

FIG. 8 is an example of a typical plasma flame generated by an exemplary inventive hand-piece. As shown in FIG. 8, when assembled and turned on, a brush-like plasma flame, 11, can be generated at the tip opening, 103, of the tip member, 100. The plasma flame, 11, is stable, focused, and a bending curve of the tip member, 100, facilitates the delivery of the flame to an intended surface.

Studies have been done to assess plasma variations due to the differences on the generation parameters, including the operating currencies, carrier-gas and/or reactive-gas flow rates, and the mixing methods (such as pre-mixing or in-situ mixing with the reactive-gas passage unit) of the carrier-gas and the reactive-gas. In the pre-mixing methods, the carrier-gas and the reactive-gas may be pre-mixed before they are delivered to the hand-piece, 10. In the in-situ mixing method, the carrier-gas and the reactive-gas may be mixed at the plasma-flame generating spot, i.e., the area between the tips of electrodes. The study results show that the temperature and the spectra intensity of the resulting plasma flame vary depending on the generation parameters.

General testing protocol: The plasma brush hand piece according to an embodiment of the disclosure is operated at 4 to 10 mA using the Spellman HV power supply SL60 (Spellman High Voltage Electronics Corporation, USA). The carrier-gas utilized in the process is high purity argon gas (AR UPC300, 99.999% pure, Airgas, USA). An argon flow rate of 3000 standard cubic centimetre per minutes (sccm) is chosen for generating near body-temperature plasma flame or torch based on our previous experiments. Reactive-gas utilized is oxygen ($O_2$) (OX UHP300, 99.994% pure, Airgas, USA), with a flow rate ranging from 0 to 120 sccm. The mass flow rate of both argon and oxygen gases is regulated by using mass flow controllers (MKS Instruments Inc., USA). In addition, argon and oxygen can be mixed by two different methods: i) pre-mixing the gases before reaching the brush hand piece, and ii) in-situ mixing oxygen via the reactive-gas line near the tip opening or nozzle. Therefore, 48 different plasma conditions have been tested per various plasma parameters.

The temperature of the resulting plasma flame is measured with a digital thermometer (Omega HH 12B). An optical emission spectroscopy (OES) unit, Acton 2750 (Princeton Instruments, USA), is utilized to observe the light emitted from the plasma flame. The system is calibrated by using IntelliCal™ for wavelength. For the study, the grating utilized is 150 grooves per millimetre with a blazing wavelength of 500 nm. Spectra are acquired from 200 nm to 900 nm in a Step and Glue mode. The results are normalized by comparing with the spectra without oxygen addition.

Table 1 summarizes the temperature profile with various oxygen flow rates and electrical current levels when different oxygen mixing methods is applied. The results indicate that i) the plasma temperature increases gradually as the electric current or larger oxygen flow rate increases, and ii) the temperature in the pre-mixing group is systematically higher than that in the in-situ mixing group.

TABLE 1

Plasma Temperature Variations Per Generation Parameters

| In-situ Mix | Temperature (° C.) Reactive-gas (sccm) | | | | | |
|---|---|---|---|---|---|---|
| Current | 0 $O_2$ | 15 $O_2$ | 30 $O_2$ | 60 $O_2$ | 90 $O_2$ | 120 $O_2$ |
| 4 mA | 29 | 29.1 | 29.5 | 29.4 | 29.5 | 29.5 |
| 6 mA | 31.4 | 31.5 | 32 | 31.8 | 32 | 32 |
| 8 mA | 33.8 | 34 | 34.1 | 34.2 | 34.4 | 34.6 |
| 10 mA | 35.6 | 35.5 | 35.6 | 36 | 36.2 | 36.4 |

| Pre-mix | Temperature (° C.) Reactive-gas (sccm) | | | | | |
|---|---|---|---|---|---|---|
| Current | 0 $O_2$ | 15 $O_2$ | 30 $O_2$ | 60 $O_2$ | 90 $O_2$ | 120 $O_2$ |
| 4 mA | 29.6 | 30.3 | 32 | 32.3 | 32.3 | 32.4 |
| 6 mA | 34.5 | 35.2 | 36.8 | 36.8 | 36.8 | 37.1 |
| 8 mA | 34.2 | 40.4 | 41.5 | 41.6 | 42.2 | 42.8 |
| 10 mA | 36.6 | 47 | 46.7 | 48.8 | 48.6 | 48.8 |

During the testing, it is further observed that the in-situ mixing method can hold more oxygen flow than the pre-mixing method under the similar conditions. During the tests applying the pre-mixing method, the plasma flame is observed to be unstable (or flicking) with high oxygen flow, which results unreliable OES data. After OES data is collected, oxygen (O) species are analysed at 777.2 nm and 844.6 nm. Hydroxyl (OH) species are analysed at 309 nm. Peaks at 714.7 nm were also selected for Ar species.

Figure 9:
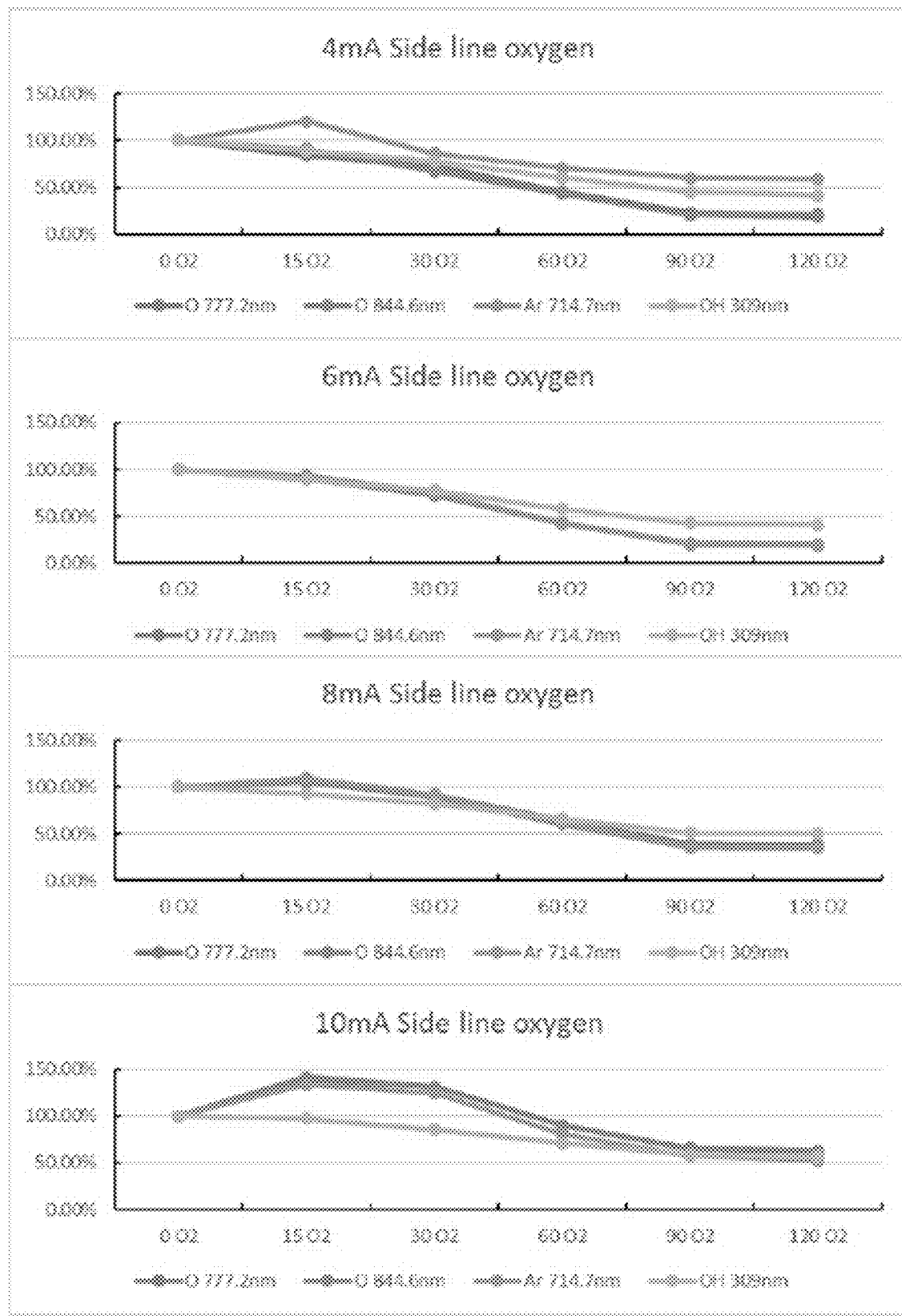
FIG. 9 includes the graphs of spectra intensity analyses of plasma flames generated under an in-situ mixing method.
Figure 10:
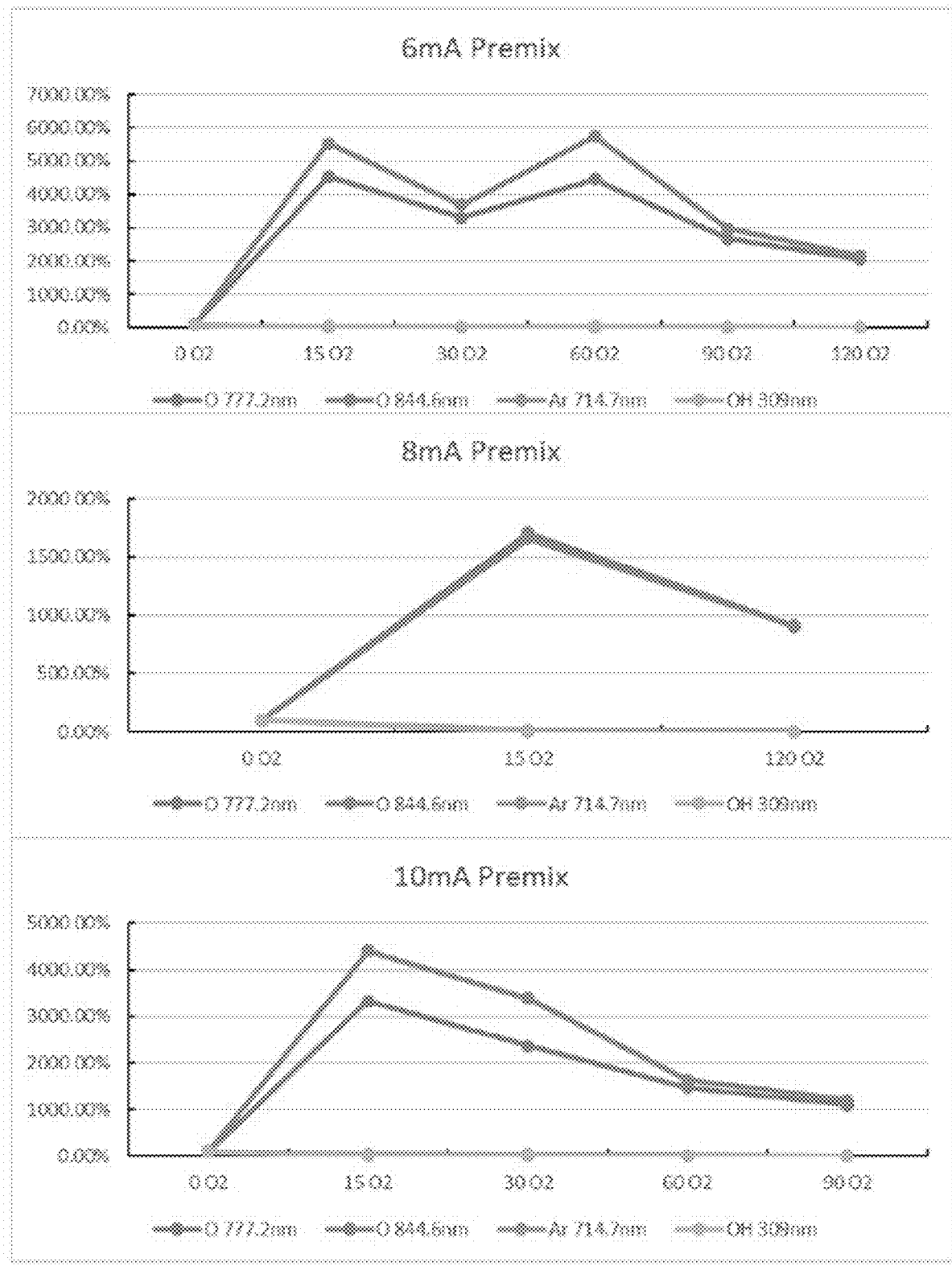
FIG. 10 includes the graphs of spectra intensity analyses of plasma flames generated under a pre-mixing method.

FIGS. 9 and 10 are graphs of spectra intensity analyses of plasma flames generated under different parameters and mixing methods. FIG. 9 compiles the graphs of spectra intensity analyses of plasma flames generated under the in-situ mixing method, while FIG. 10 is under the pre-mixing method. Tables 3 and 4 summarize the spectra intensity data of FIGS. 9 and 10, respectively.

TABLE 2

Intensity Ratio under In-situ Mixing Method

| Ratio | (intensity of X $O_2$)/(intensity of 0 $O_2$) | | | | | |
|---|---|---|---|---|---|---|
| | 0 $O_2$ | 15 $O_2$ | 30 $O_2$ | 60 $O_2$ | 90 $O_2$ | 120 $O_2$ |
| 4 mA | | | | | | |
| O 777.2 nm | 100.00% | 84.00% | 72.80% | 45.24% | 22.90% | 21.28% |
| O 844.6 nm | 100.00% | 90.62% | 67.30% | 43.11% | 20.67% | 19.21% |
| Ar 714.7 nm | 100.00% | 120.41% | 86.30% | 70.54% | 59.95% | 59.17% |
| OH 309 nm | 100.00% | 89.33% | 77.78% | 60.00% | 45.33% | 41.78% |
| 6 mA | | | | | | |
| O 777.2 nm | 100.00% | 89.71% | 72.39% | 42.91% | 21.46% | 20.25% |
| O 844.6 nm | 100.00% | 90.32% | 73.12% | 42.49% | 20.38% | 18.93% |
| Ar 714.7 nm | 100.00% | 94.20% | 75.39% | 42.29% | 21.04% | 19.09% |
| OH 309 nm | 100.00% | 89.33% | 77.78% | 57.78% | 43.11% | 41.33% |
| 8 mA | | | | | | |
| O 777.2 nm | 100.00% | 108.41% | 91.49% | 64.35% | 38.73% | 38.19% |
| O 844.6 nm | 100.00% | 104.81% | 88.83% | 60.58% | 35.84% | 35.10% |
| Ar 714.7 nm | 100.00% | 109.26% | 91.08% | 62.19% | 35.46% | 34.95% |
| OH 309 nm | 100.00% | 92.89% | 81.86% | 66.42% | 51.23% | 50.74% |
| 10 mA | | | | | | |
| O 777.2 nm | 100.00% | 139.05% | 131.12% | 89.85% | 65.76% | 63.09% |
| O 844.6 nm | 100.00% | 141.65% | 131.39% | 89.30% | 64.34% | 61.48% |
| Ar 714.7 nm | 100.00% | 133.70% | 124.62% | 80.94% | 57.53% | 52.68% |
| OH 309 nm | 100.00% | 97.14% | 85.69% | 70.80% | 58.97% | 56.30% |

TABLE 3

Intensity Ratio under Pre-mixing Method (intensity of X $O_2$)/(intensity of 0 $O_2$)

| Ratio | 0 $O_2$ | 15 $O_2$ | 30 $O_2$ | 60 $O_2$ | 90 $O_2$ | 120 $O_2$ |
|---|---|---|---|---|---|---|
| 4 mA | | | | | | |
| O 777.2 nm | 100.00% | | Plasma flame is not stable | | | |
| O 844.6 nm | 100.00% | | | | | |
| Ar 714.7 nm | 100.00% | | | | | |
| OH 309 nm | 100.00% | | | | | |
| 6 mA | | | | | | |
| O 777.2 nm | 100.00% | 4535.16% | Plasma flame is not stable | | | |
| O 844.6 nm | 100.00% | 5529.76% | | | | |
| Ar 714.7 nm | 100.00% | 38.35% | | | | |
| OH 309 nm | 100.00% | 0.00% | | | | |
| 8 mA | | | | | | |
| O 777.2 nm | 100.00% | 1702.15% | 1474.54% | 1293.87% | Plasma flame is not stable | |
| O 844.6 nm | 100.00% | 1658.78% | 1398.65% | 1252.03% | | |
| Ar 714.7 nm | 100.00% | 13.07% | 11.43% | 0.00% | | |
| OH 309 nm | 100.00% | 0.00% | 0.00% | 0.00% | | |
| 10 mA | | | | | | |
| O 777.2 nm | 100.00% | 3335.55% | 2361.67% | 1477.13% | 1102.78% | Plasma flame is not stable |
| O 844.6 nm | 100.00% | 4409.65% | 3390.68% | 1625.08% | 1201.61% | |
| Ar 714.7 nm | 100.00% | 40.24% | 22.77% | 9.40% | 7.00% | |
| OH 309 nm | 100.00% | 0.00% | 0.00% | 0.00% | 0.00% | |

Under both reactive-gas mixing methods, OES data of the plasma flame does not indicate significantly more reactive oxygen species generated than the plasma flame with only carrier-gas (only small amount of monatomic oxygen has been observed at 777.2 nm and 844.6 nm). When introducing oxygen, little change on frequencies and amount of oxygen peaks has been detected between the pre-mixing and the in-situ mixing methods. However, the intensities of oxygen peaks increase sharply when employing the pre-mixing method, which indicates more reactive oxygen species might be produced. Besides oxygen species, OH species also have been observed at 309 nm under both methods. Under the in-situ mixing method, OH species diminish gradually, whereas under the pre-mixing method, the peaks of OH disappear immediately when introducing the oxygen, which may be explained that the OH species are consumed by the excess amount of reactive oxygen species being produced under the pre-mixing method.

In conclusion, the in-situ mixing method (with the reactive-gas passage unit) provides similar reactive species in the resulting plasma flame as those with the pre-mixing method. Advantageously, a stable plasma flame with low temperature can be generated under relatively low current but high reactive-gas (such as oxygen) flow rate by employing the in-situ mixing method.

Figure 11A:
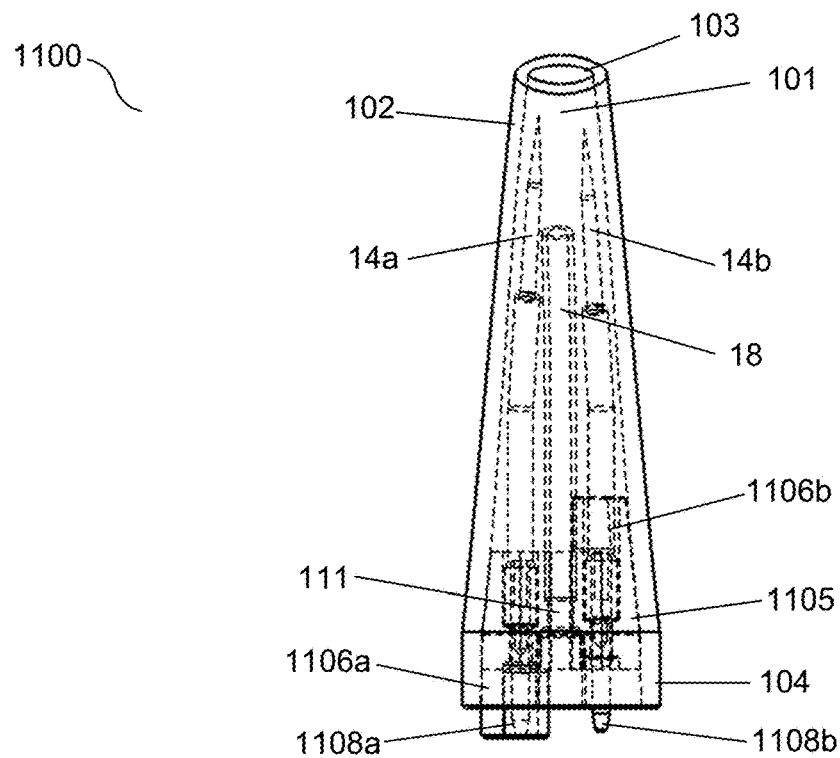
FIG. 11A is a front-view transparent illustration of an exemplary tip member, according to an embodiment of the present disclosure.
Figure 11B:
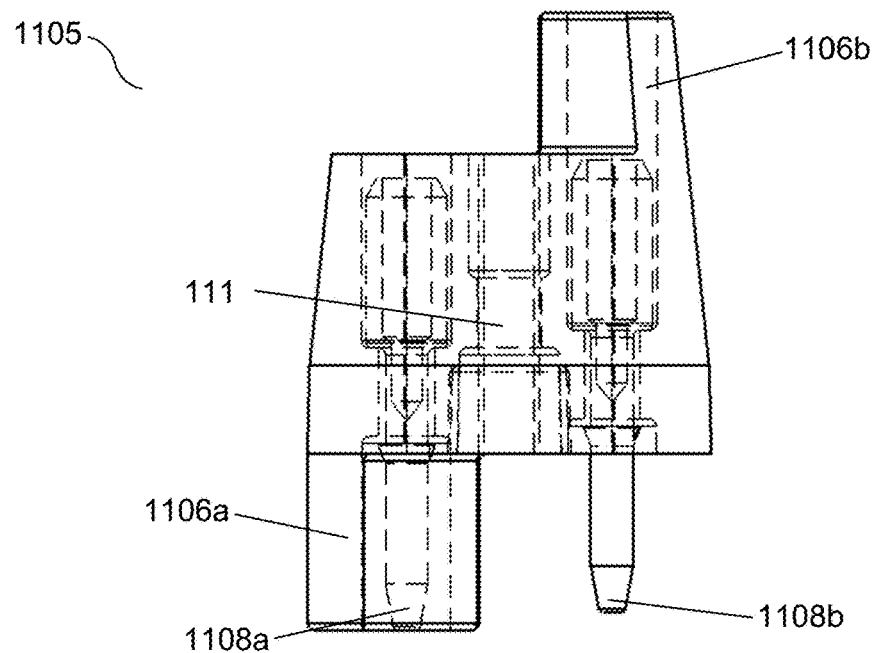
FIG. 11B is a front-view transparent illustration of an exemplary tip insert included in the tip member illustrated in FIG. 11B.

FIG. 11A is a front-view transparent illustration of an exemplary tip member, according to an embodiment of the present disclosure. FIG. 11B is a front-view transparent illustration of an exemplary tip insert included in the tip member illustrated in FIG. 11B.

As shown in FIGS. 11A and 11B, the tip member, 1100, includes a) a tip shell, 102, in a hollow conical shape forming a tip chamber, 101, with a narrow tip opening, 103, and a wide tip base end, 104, and b) a tip insert, 1105, snugly fitted inside of the tip base end, 104. The tip insert, 1105, further includes first and second extended electrode slots, 1106a/b, for attaching the electrodes, 14a/b, a first carrier-gas opening (not shown), and a first reactive-gas slot, 111, for attaching a distal reactive-gas tube, 18, and allowing the distal reactive-gas tube to connect with a proximate reactive-gas tube (not shown). The second extended electrode slot, 1106b, which is formed as a plastic sleeve, extends in a direction along an extending direction of the conical shell, 102, and towards the tip opening, 103, for holding the cathode, 14b. The first extended electrode slot, 1106a, which is formed as a plastic sleeve, extends in a direction opposite to the extending direction of the second extended electrode slot, 1106b, and towards a shaft member, for holding the grounded electrode, 14a. The tip member, 1100, further includes a first pair of electric connectors, 1108a/b for connecting the electrodes to their respective electric lines (not shown). The electric connector, 1108a, is inserted in the extended electrode slot, 1106a. The electric connector, 1108b, protrudes out of the tip insert, 1105, towards the shaft member, to be connected with an electric connector of the shaft member. The extended electrode slots, 1106a/b, increases the air clearance and creepage distance between two electrodes, 14a/b. With a larger air clearance and creepage distance, the dielectric strength level is improved to provide better reliability and electric insulation.

Figure 12A:
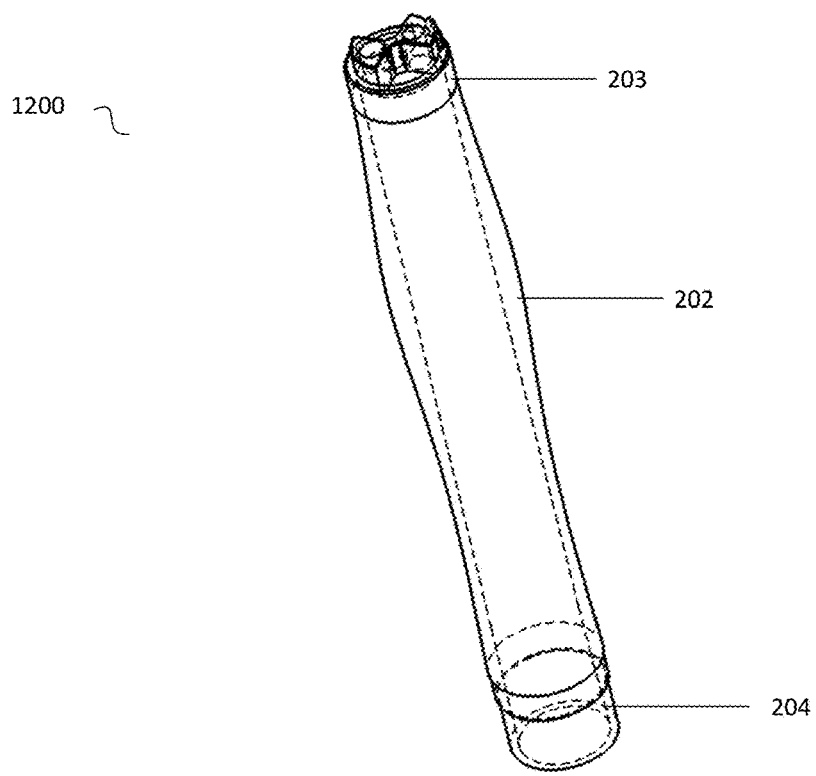
FIG. 12A is a 3-D transparent illustration of an exemplary shaft member, according to an embodiment of the present disclosure.
Figure 12B:
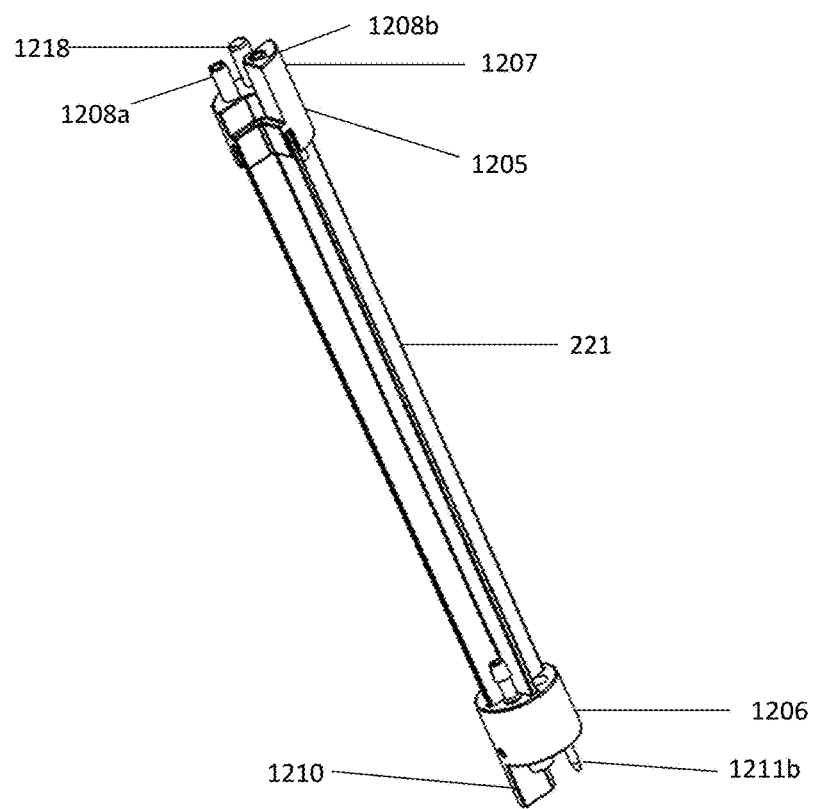
FIG. 12B is a 3-D illustration of an exemplary shaft-tip insert, an exemplary shaft-connector insert, and an exemplary partition unit, included in the shaft member of FIG. 12A, according to an embodiment of the present disclosure.
Figure 12C:
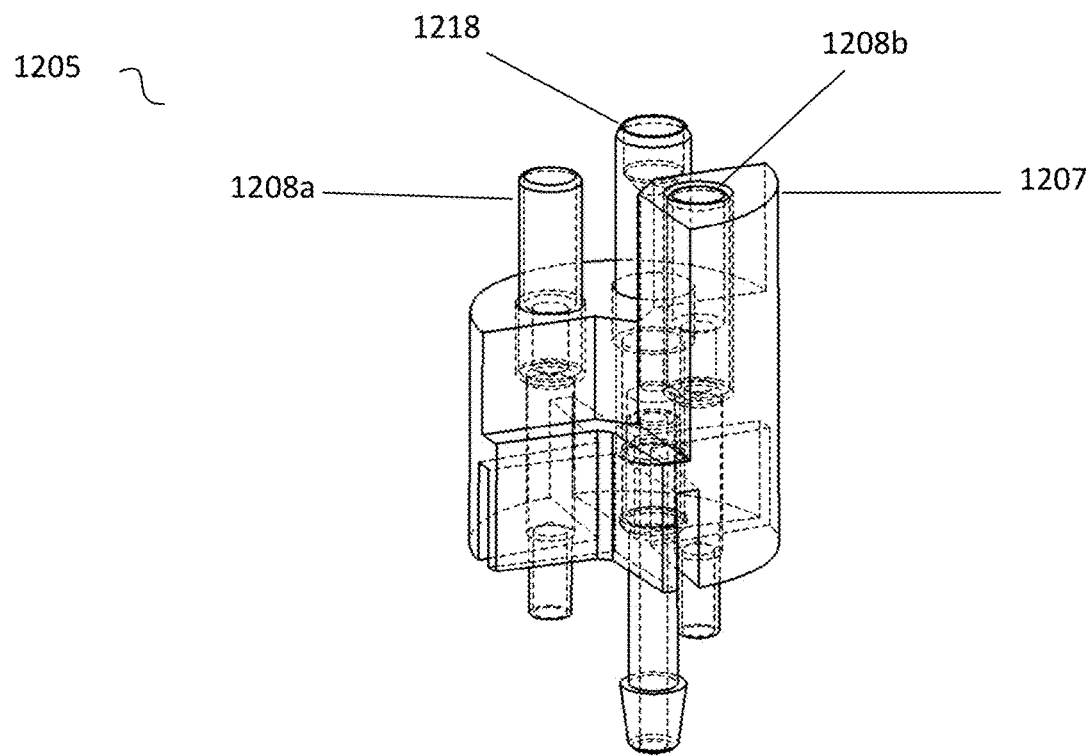
FIG. 12C is a 3-D transparent illustration of the exemplary shaft-tip insert of FIG. 12B, according to an embodiment of the present disclosure.
Figure 12D:
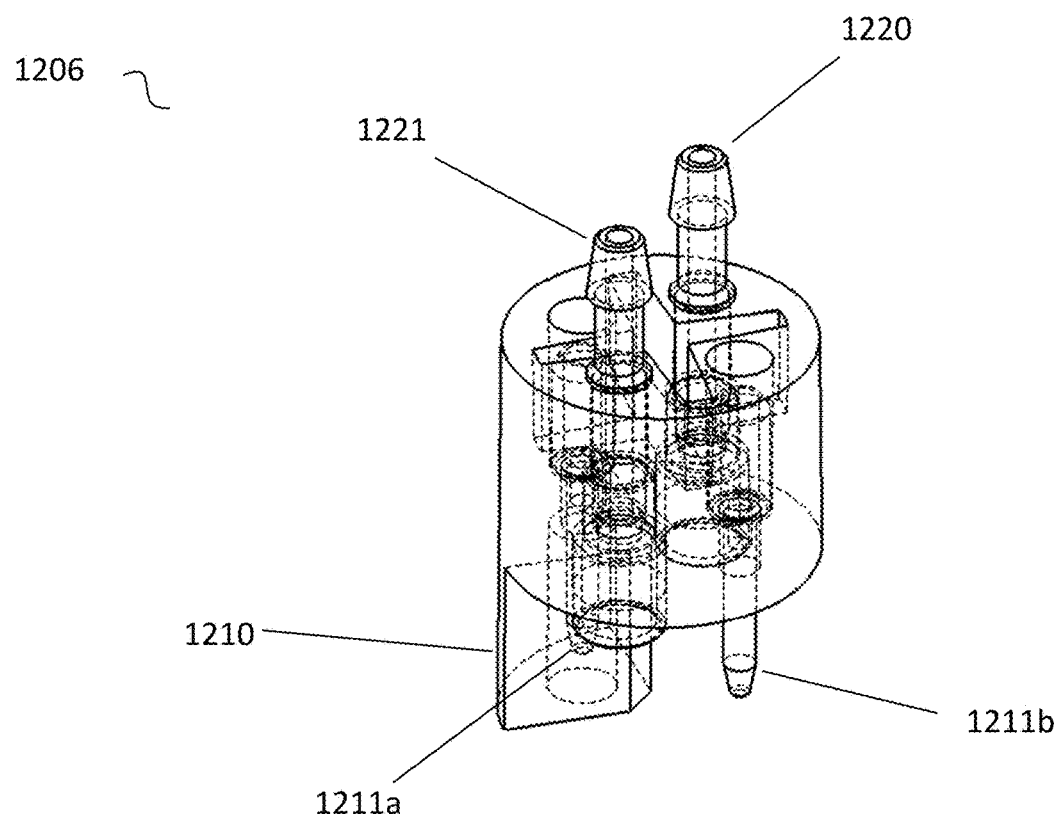
FIG. 12D is a 3-D transparent illustration of the exemplary shaft-connector insert of FIG. 12B, according to an embodiment of the present disclosure.

FIG. 12A is a 3-D transparent illustration of an exemplary shaft member, according to an embodiment of the present disclosure. FIG. 12B is a 3-D illustration of an exemplary shaft-tip insert, an exemplary shaft-connector insert, and an exemplary partition unit, included in the shaft member of FIG. 12A, according to an embodiment of the present disclosure. FIG. 12C is a 3-D transparent illustration of the exemplary shaft-tip insert of FIG. 12B, according to an embodiment of the present disclosure. FIG. 12D is a 3-D transparent illustration of the exemplary shaft-connector insert of FIG. 12B, according to an embodiment of the present disclosure.

As shown in FIGS. 12A to 12D, the shaft member, 1200, includes a) a shaft chamber shell, 202, in an elongated tubular shape (optionally ergonomically modified for better gripping and handling by a user), forming a shaft chamber, with a shaft-tip end, 203, to be attached to a tip member (e.g., the tip member, 1100), and a shaft-connector end, 204, to be attached to a tubing connection member, b) a shaft-tip insert, 1205, fitted inside of the shaft-tip end, 203, and c) a shaft-connector insert, 1206, fitted inside of the shaft-connector end, 204.

The shaft-tip insert, 1205, further includes an extended electrode slot, 1207, a pair of electric connectors, 1208*a/b*, inserted therein, and a reactive-gas fitting unit, 218. The extended electrode slot, 1207, is formed as a plastic sleeve and extends in the extending direction of the shaft member, 1200, towards the tip member, 1100, to be attached to the shaft-tip end, 203. The electric connector, 1208*a*, protrudes out of the shaft-tip insert, 1205, towards the tip member, 1100, to be connected with the electric connector, 1108*a*, of the tip member, 1100. The electric connector, 1208*b*, to be connected with the electric connector, 1108*b*, of the tip member, 1100, is inserted inside of the extended electrode slot, 1207. The shaft-tip insert, 1205, increases the air clearance and creepage distance between the two electric connectors, 1208*a/b*, thus improving electric insulation between the two electric connectors, 1208*a/b*.

The shaft-connector insert, 1206, further includes an extended electrode slot, 1210, a pair of electric connectors, 1211*a/b*, a reactive-gas fitting unit, 1220, and a carrier-gas fitting unit, 1221. The extended electrode slot, 1210, is formed as a plastic sleeve and extends in the extending direction of the shaft member, 1200, towards the tubing connection member to be attached to the shaft-connector end, 204. The electric connector, 1211*a*, is inserted inside of the extended electrode slot, 1210. The electric connector, 1211*b*, protrudes out of the shaft-connector insert, 1206, towards the tubing connection member. The shaft-connector insert, 1206, increases the air clearance and creepage distance between the two electric connectors, 1211*a/b*, thus improving electric insulation between the two electric connectors, 1211*a/b*.

Figure 13A:
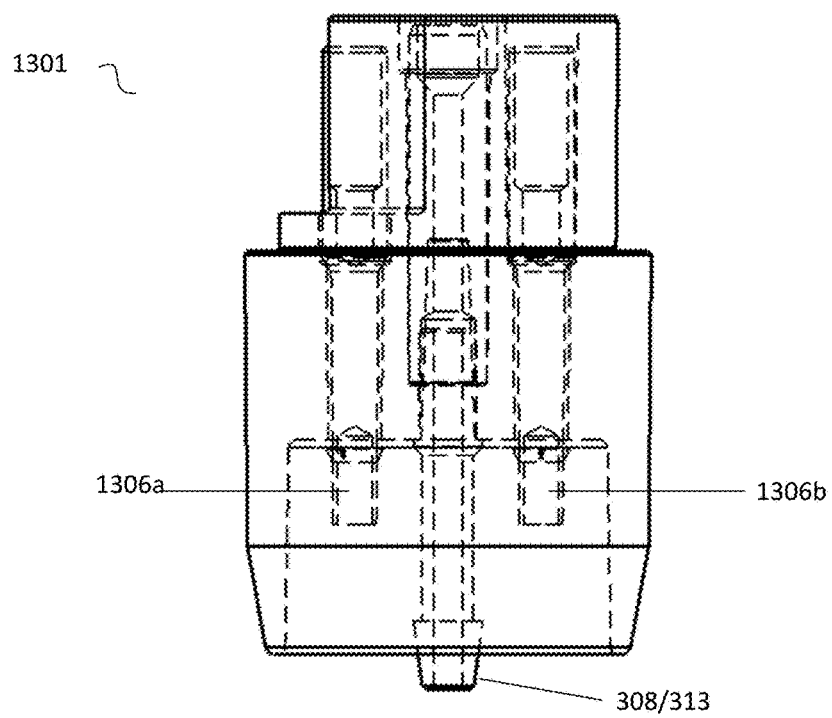
FIG. 13A is a transparent illustration of an exemplary source connector included in an exemplary tubing connection member, according to an embodiment of the present disclosure.
Figure 13B:
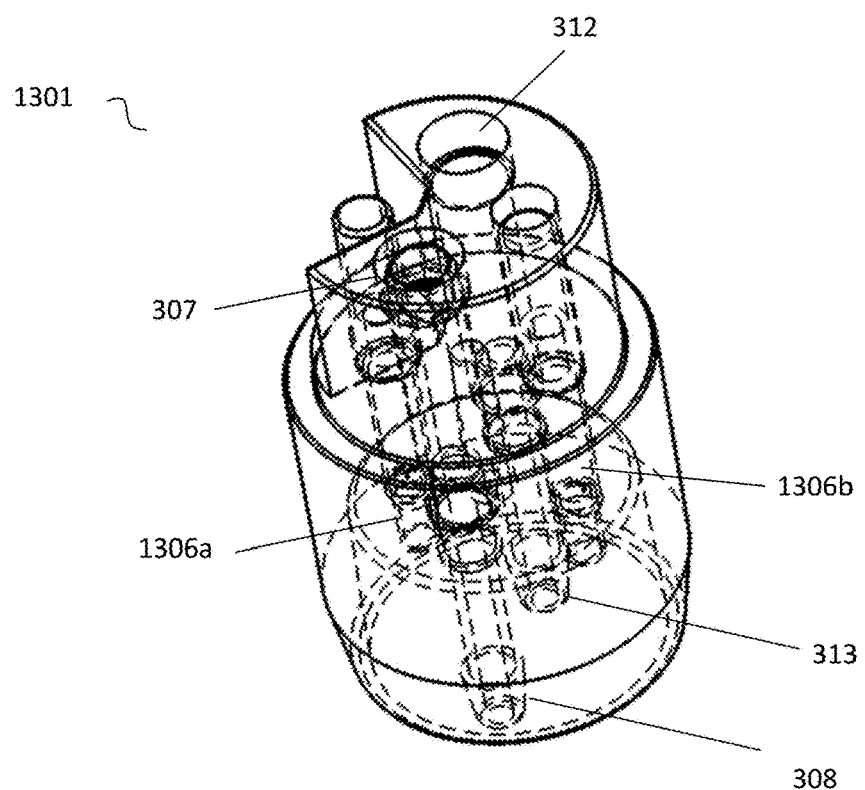
FIG. 13B is a 3-D transparent illustration of the exemplary source connection of FIG. 13A.

FIG. 13A is a transparent illustration of an exemplary source connector included in an exemplary tubing connection member, according to an embodiment of the present disclosure. FIG. 13B is a 3-D transparent illustration of the exemplary source connection of FIG. 13A.

As shown in FIGS. 13A and 13B, the source connector, 1301, includes a pair of electric connectors, 1306*a/b*, a carrier-gas opening, 307, a reactive-gas slot, 312, a carrier-gas fitting unit, 308, and a reactive-gas fitting unit, 313. The carrier-gas fitting unit, 308, is inserted within the carrier-gas opening, 307. The reactive-gas fitting unit, 313, is inserted in the reactive-gas slot, 312. The electric connector, 1306*a*, is connected with the electric connector, 1211*a*, of the shaft member, 1200. The electric connector, 1306*b*, is connected with the electric connector, 1211*b*, of the shaft member, 1200.

Figure 14A:
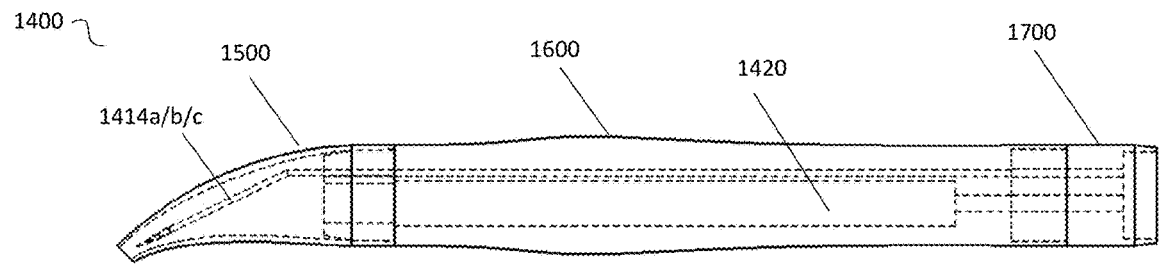
FIG. 14A is a side-view transparent illustration of an exemplary hand piece with three electrodes, according to an embodiment of the present disclosure.
Figure 14B:
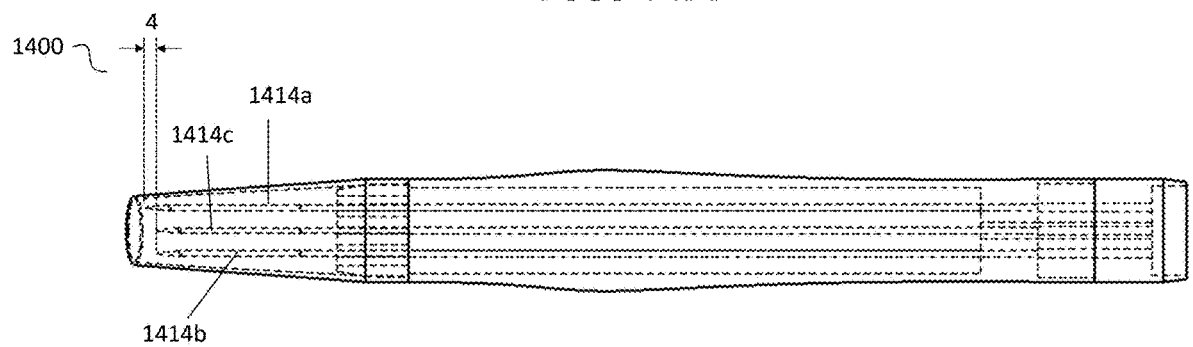
FIG. 14B is a transparent illustrated (top view) of the exemplary hand piece of FIG. 14A, according to an embodiment of the present disclosure.
Figure 14C:
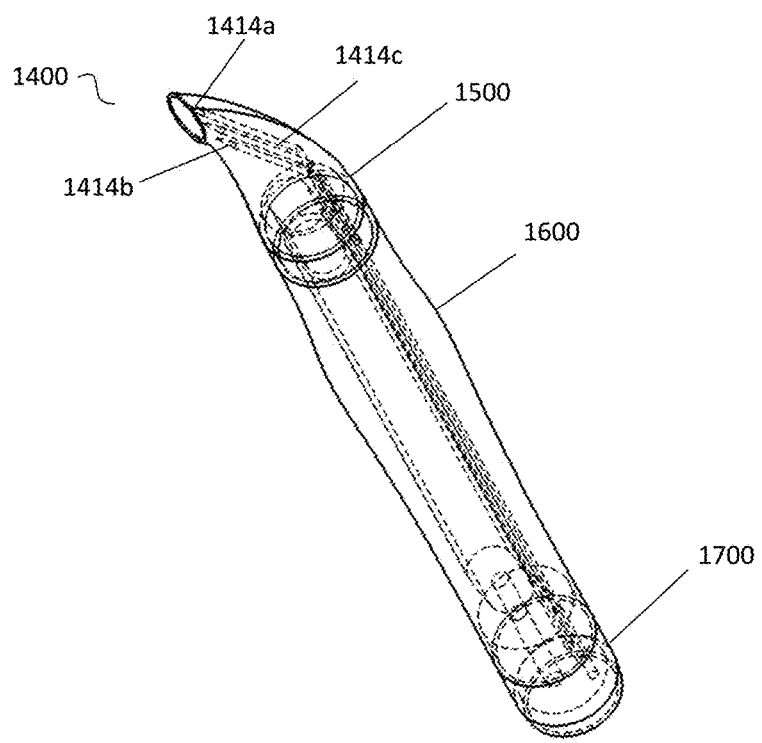
FIG. 14C is a 3-D transparent illustration of the exemplary hand piece of FIG. 14A, according to an embodiment of the present disclosure.

FIG. 14A is a side-view transparent illustration of an exemplary hand piece with three electrodes, according to an embodiment of the present disclosure. FIG. 14B is a transparent illustrated (top view) of the exemplary hand piece of FIG. 14A, according to an embodiment of the present disclosure. FIG. 14C is a 3-D transparent illustration of the exemplary hand piece of FIG. 14A, according to an embodiment of the present disclosure.

As shown in FIGS. 14A to 14C, the hand piece, the hand-piece, 1400, includes a segmented housing member with three main segments, a tip member, 1500, a shaft member, 1600, and a tubing connection member, 1700. The tip member, 1500, is formed in a hollow conical shape, optionally bent or curved for targeted and localized delivery (especially for hard to reach areas). The shaft member, 1600, is formed in an elongated tubular shape, optionally curved to facilitate easy grasping or holding by a user. The tubing connection member, 1700, provides easy connections to a power source and plasma gas supplies. The hand-piece, 1400, further includes a grounded electrode (anode), 1414*a*, a high voltage electrode, 1414*b*, and a trigger electrode, 1414*c*. The trigger electrode, 1414*c*, is placed between the grounded electrode, 1414*a*, and the high voltage electrode, 1414*b*, and at the same or similar vertical level as the high voltage electrode, 1414*b*, with a desired vertical-level difference, 4, apart from the grounded electrode, 1414*a*. The hand-piece, 1400, further includes a carrier-gas chamber, 1420.

Figure 15A:
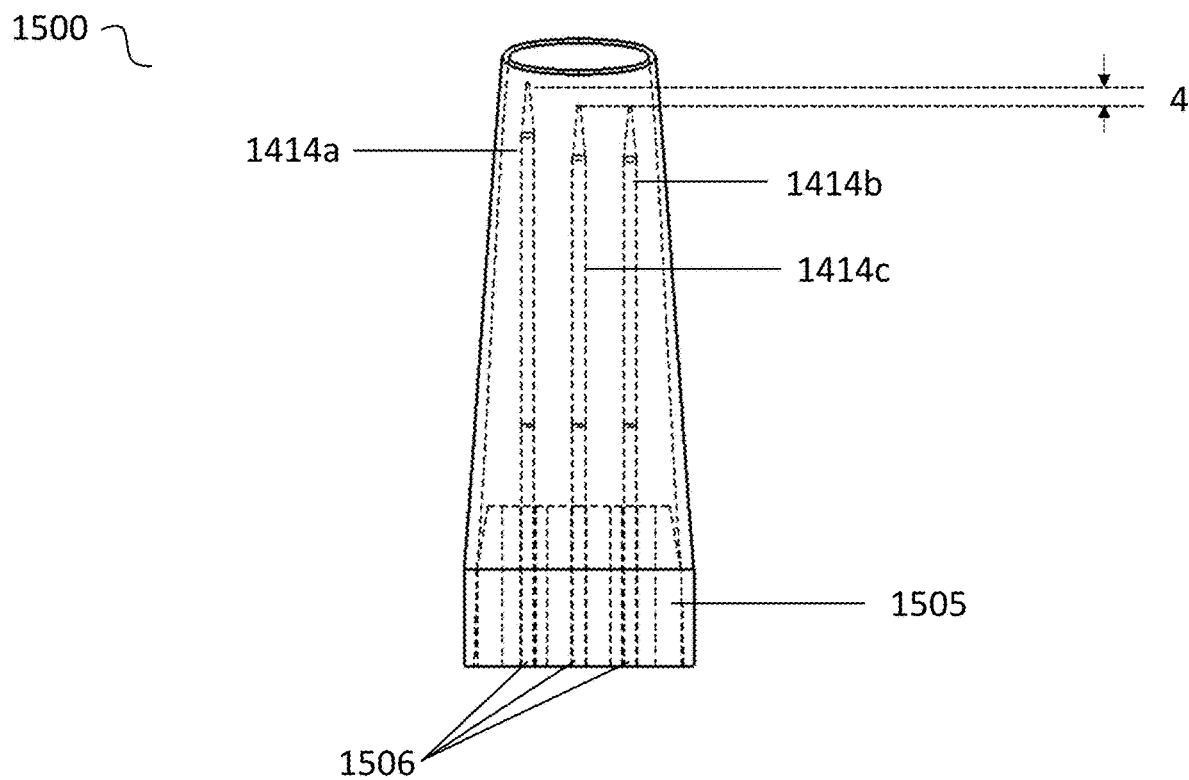
FIG. 15A is a front-view transparent illustration of an exemplary tip member, according to an embodiment of the present disclosure.
Figure 15B:
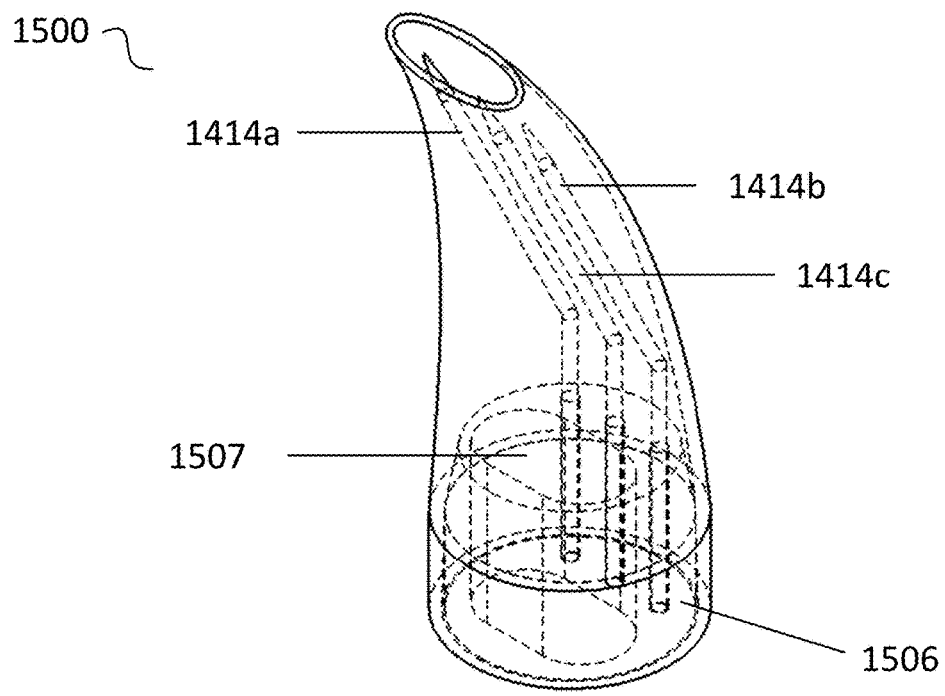
FIG. 15B is a 3-D transparent illustration of the exemplary tip member of FIG. 15A, according to an embodiment of the present disclosure.

FIG. 15A is a front-view transparent illustration of an exemplary tip member, according to an embodiment of the present disclosure. FIG. 15B is a 3-D transparent illustration of the exemplary tip member of FIG. 15A, according to an embodiment of the present disclosure.

As show in FIGS. 15A and 15B, the tip member, 1500, includes a tip insert, 1505, snugly fitted inside of one end of the tip member, 1500. The tip insert, 1505, in a conical-frustum-like shape, includes three electrode slots, 1506, for attaching the grounded electrode, 1414*a*, the high voltage electrode, 1414*b*, and the trigger electrode, 1414*c*, respectively. The trigger electrode, 1414*c*, is placed at the same or similar vertical level as the high voltage electrode, 1414*b*, with the desired vertical-level difference, 4, apart from the grounded electrode, 1414*a*. The tip insert, 1505, further includes a carrier-gas opening 1507, for allowing the plasma carrier-gas to flow to a tip chamber.

Figure 16:
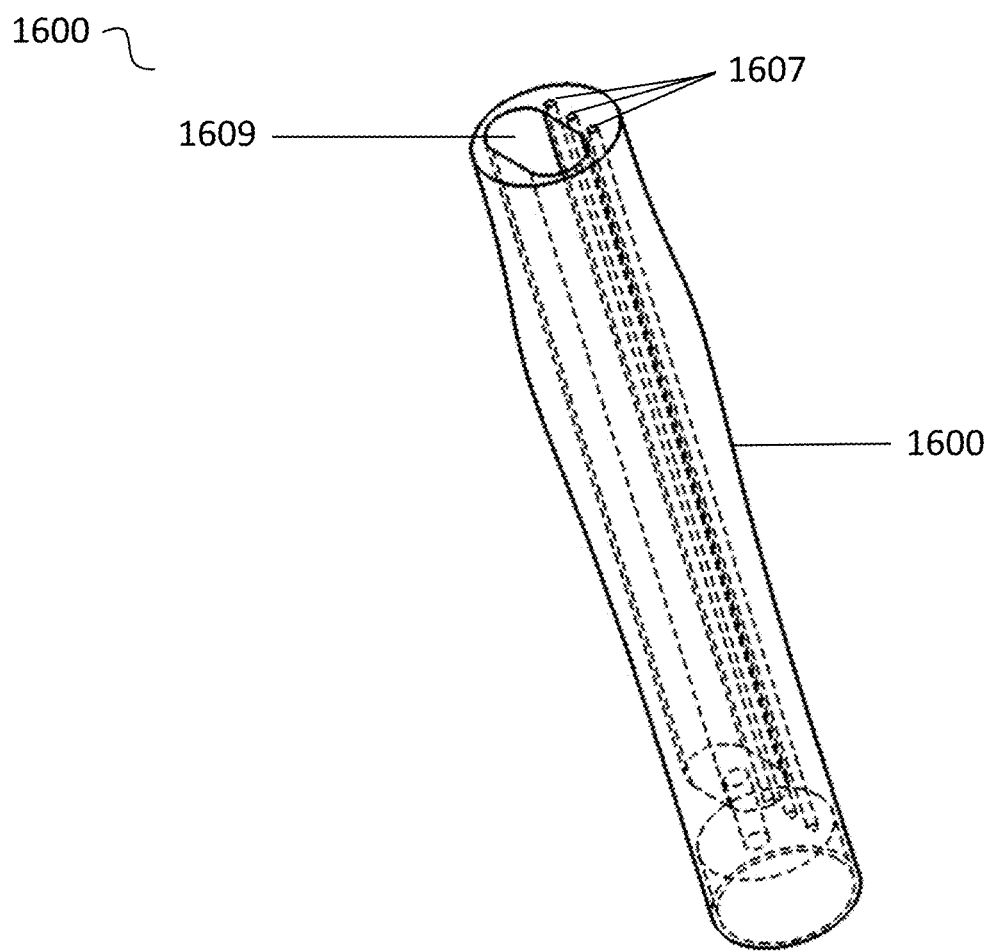
FIG. 16 is a 3-D transparent illustration of an exemplary shaft member, according to an embodiment of the present disclosure.

FIG. 16 is a 3-D transparent illustration of an exemplary shaft member, according to an embodiment of the present disclosure. As shown in FIG. 16, the shaft member, 1600, includes three electrode slots, 1607, for attaching electric lines disposed inside of the shaft member, 1600, and electrically connecting the electric lines to the the grounded electrode, 1414*a*, the high voltage electrode, 1414*b*, and the trigger electrode, 1414*c*, respectively. The shaft member, 1600, further includes a carrier-gas opening, 1609, matching the carrier-gas opening, 1507, of the tip member, 1500, to facilitate the carrier-gas passage.

Figure 17:
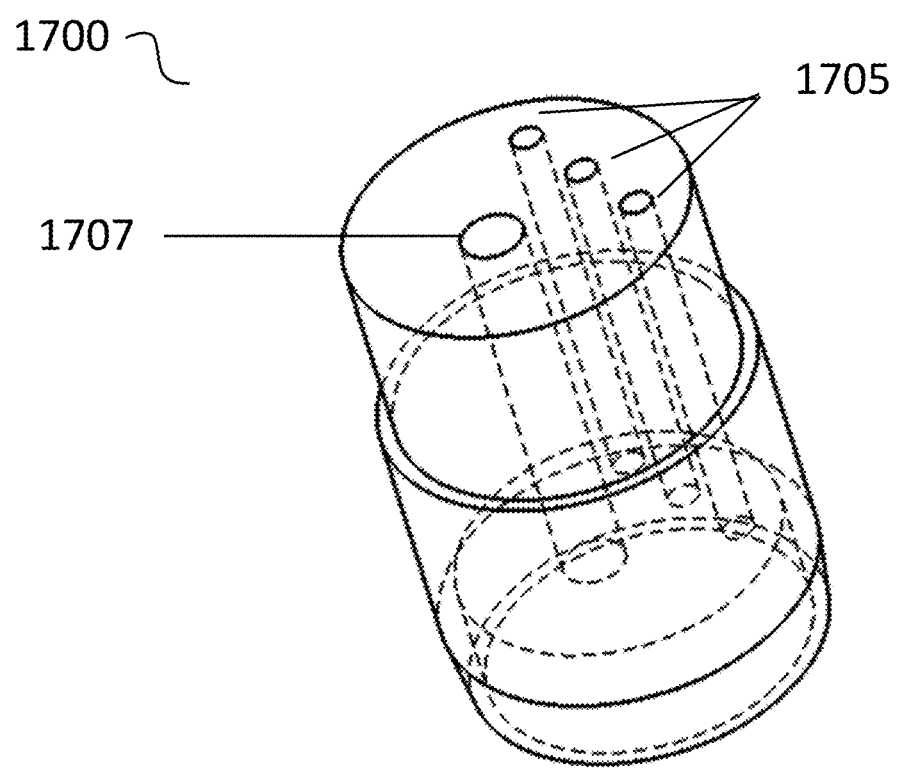
FIG. 17 is a 3-D transparent illustration of an exemplary tubing connection member, according to an embodiment of the present disclosure.

FIG. 17 is a 3-D transparent illustration of an exemplary tubing connection member, according to an embodiment of the present disclosure. As shown in FIG. 17, the tubing connection member, 1700, includes three electrode slots, 1705, for electrically connecting electric lines disposed inside of the tubing connection member, 1700, to a power source (e.g., power source, 15, of FIG. 3B). The tubing connection member, 1700, further includes and a carrier-gas opening, 1707, matching the carrier-gas opening, 1609, of the shaft member, 1600, to facilitate the passage of the plasma carrier-gas supplied from a plasma carrier-gas supply (e.g., plasma carrier-gas supply, 16, of FIG. 3B).

While illustrative embodiments have been described herein, the scope of the present disclosure covers any and all embodiments having equivalent elements, modifications, omissions, combinations (e.g., of aspects across various embodiments), adaptations and/or alterations as would be appreciated by those skilled in the art based on the present disclosure. For example, features included in different embodiments shown in different figures may be combined. The limitations in the claims are to be interpreted broadly based on the language employed in the claims and not limited to examples described in the present specification or during the prosecution of the application. The examples are to be construed as non-exclusive. It is intended, therefore, that the specification and examples be considered as illustrative only, with a true scope and spirit being indicated by the following claims and their full scope of equivalents.

What is claimed is:

1. A device, when connected with a power source and a carrier-gas supply, for generating and delivering a plasma flame to a site, the device comprising:
 a housing member configured to provide for gas passage, the housing member having a tip member with a tip opening at its distal end, a shaft member at its middle section, and a tubing connection member at its proximate end;
 a plurality of electric lines housed in the shaft member and connectable to the power source via the tubing connection member; and
 a plurality of electrodes including a grounded electrode and at least one high voltage electrode, the plurality of electrodes being contained in the tip member and being attachable to the plurality of electric lines, and
 wherein when the device is connected to the power source and the carrier-gas supply, the carrier-gas flows from the carrier-gas supply, via the tubing connection member and the shaft member, to the tip member and is excited by the plurality of electrodes to generate the plasma flame at the tip opening,
 wherein the tip member further comprises:
 a tip shell in a hollow conical shape forming a tip chamber having a narrow distal end and a wide base end, wherein the tip opening is at the narrow distal end; and
 a tip insert fitted at the base end, wherein the tip insert further comprises a first carrier-gas opening for passage of carrier-gas, and a plurality of electrode slots for attaching the electrodes and connecting the electrodes to their respective electric lines.

2. The device of claim 1, wherein a tip of the grounded electrode and a tip of the at least one high-voltage electrode have a vertical-level difference.

3. The device of claim 2, wherein a distance between the tip of the grounded electrode and the tip opening is shorter than a distance between the tip of the at least one high-voltage electrode and the tip opening.

4. The device of claim 1, wherein the housing member is formed in one piece.

5. The device of claim 1, wherein the housing member is segmented and attachable.

6. The device of claim 1, wherein the tip insert is formed in a conical-frustum-like shape.

7. The device of claim 1, wherein the shaft member further comprises:
 a shaft shell in an elongated tubular shape forming a shaft chamber with a shaft-tip end and a shaft-connector end;
 a shaft-tip insert fitted at the shaft-tip end, having a second carrier-gas opening for passage of carrier-gas, and a first set of electric slots for attaching the electric lines and connecting the electric lines to their respective electrodes; and
 a shaft-connector insert fitted at the shaft-connector end, having a third carrier-gas opening for the passage of carrier-gas, and a second set of electric slots for attaching the electric lines and connecting the electric lines to the tubing connection member,
 wherein the shaft member is configured to attach to the tip member at the shaft-tip end and to the tubing connection member at the shaft-connector end.

8. The device of claim 7, further comprising a partition unit inserted between the shaft-tip insert and the shaft-connector insert.

9. The device of claim 7, wherein the tubing connection member further comprises:
 a source connector with an adaptor end and a tubing end; and
 a connector collet,
 wherein the adaptor end is configured for insertion into the shaft-connector end of the shaft member, while the tubing end connects to a source tubing, to provide connections between the electric lines and the power source and between a gas passage unit to the gas supply, and
 wherein the connector collet is configured to slide over the source connector and the shaft-connector end of the shaft member to ensure a secure attachment between the source connector and the shaft member.

10. The device of claim 1, further comprising:
 a reactive-gas passage unit for generating the plasma flame with multiple gas supplies,
 wherein the reactive-gas passage unit comprises a reactive-gas tube with a proximate reactive-gas tube and a distal reactive-gas tube,
 wherein the proximate reactive gas tube is housed in the shaft member, the distal reactive gas tube is housed in the tip member, and the reactive-gas flows through the reactive-gas passage unit and be released in-situ at the tips of the electrodes to be excited with the carrier-gas.

11. The device of claim 10, wherein the reactive-gas tube is segmented but attachable.

* * * * *

UNITED STATES PATENT AND TRADEMARK OFFICE
CERTIFICATE OF CORRECTION

PATENT NO. : 10,631,396 B2
APPLICATION NO. : 15/925290
DATED : April 21, 2020
INVENTOR(S) : Meng Chen et al.

Page 1 of 1

It is certified that error appears in the above-identified patent and that said Letters Patent is hereby corrected as shown below:

In the Claims

Claim 10, Column 24, Line 44, "be released" should read as --is released--.

Signed and Sealed this
Tenth Day of November, 2020

Andrei Iancu
*Director of the United States Patent and Trademark Office*